US005567317A

United States Patent [19]
Kauvar

[11] Patent Number: 5,567,317
[45] Date of Patent: Oct. 22, 1996

[54] METHOD TO IDENTIFY ANALYTE-BINDING LIGANDS

[75] Inventor: Lawrence M. Kauvar, San Francisco, Calif.

[73] Assignee: Terrapin Technologies, Inc., South San Francisco, Calif.

[21] Appl. No.: 401,445

[22] Filed: Mar. 9, 1995

Related U.S. Application Data

[62] Division of Ser. No. 116,059, Sep. 2, 1993, Pat. No. 5,409,611, which is a division of Ser. No. 49,642, Apr. 9, 1993, Pat. No. 5,340,474, which is a continuation-in-part of Ser. No. 429,721, Oct. 31, 1989, Pat. No. 5,133,866, which is a continuation-in-part of Ser. No. 355,042, May 16, 1989, Pat. No. 4,963,263, which is a continuation of Ser. No. 172,626, Mar. 24, 1988, abandoned, and a continuation-in-part of Ser. No. 255,906, Oct. 11, 1988, Pat. No. 5,217,869.

[51] Int. Cl.$^6$ ............................................. B01D 15/08
[52] U.S. Cl. ........................ 210/635; 210/656; 436/161; 530/413
[58] Field of Search ...................... 210/635, 656, 210/658, 198.2, 502.1; 502/400, 401, 402, 403, 404; 530/413; 436/161.518; 422/70; 96/101

[56] References Cited

U.S. PATENT DOCUMENTS 4,963,263  10/1990  Kauvar ..................................... 210/635

FOREIGN PATENT DOCUMENTS

| WO8600991 | 2/1986 | WIPO | 210/198.2 |
| WO8606487 | 11/1986 | WIPO | 210/198.2 |
| WO8903430 | 4/1989 | WIPO | 210/198.2 |

OTHER PUBLICATIONS

Snyder, Introduction to Modern Liquid Chromatography John Wiley & Sons, 1979, pp. 122.
May, *Separation and Purification*, 3rd edition, 1978, (Edmond S. Perry et al., eds.), vol. 12, "Techniques of Chemistry," (New York: John Wiley, publishers), pp. 257–293.
Peterson et al., (1984) *Methods in Enzymology* 104:113–133.
Armstrong et al., (1984) *j. Chromatographic Science* 22:411–415.
Burton et al., *J. Chromatog.* (1988) 435:127–137.
Atassi et al., (1977) *J. Biological Chemistry* 252(24):8784–8787.
McCormick et al., (19840 *Biochem. J.* 224:995–1000.
Atassi, (1985) *Biochem. J.* 226:477–485.
Seiden et al., (1986) *J. Immunology* 136(2):582–587.
Roux et al., (1987) *Proc. Natl. Acad. Sci.* (USA) 84:4984–4988.
Geysen et al., (1984) *Proc. Natl. Acad. Sci* (USA) 81:3998–4002.
Houghten, (1985) *Proc. Natl. Acad. Sci.* (USA) 82:5131–5135.
Delvin et al., *Science* (1990) 249:404–405.
Scott et al., *Science* (1990) 249:404–405.
Kauvar et al., *BioTechniques* (1990) 8(2):204–207.
Shai et al., *Biochemistry* (1987) 26(3):669–675.
Atabsi et al., *J. Biological Chemistry* (1977) 252(24):8784–8787.
Atabsi, *Biochem. J.* (1985) 266:477–485.

*Primary Examiner*—Ernest G. Therkorn
*Attorney, Agent, or Firm*—Morrison & Foerster LLP

[57] ABSTRACT

The invention provides methods to obtain panels of low molecular weight polymers resulting from varying constituent monomers, which panels are systematically diverse with respect to two or more variables. The panels can be screened for members (paralogs) which are capable of specifically binding a target moiety. Such paralogs are useful for chromatographic separations and purifications of desired analytes and in binding assays, such as immunoassays, involving said analytes, as well as for any purpose which requires said specific binding. The invention also provides kits for these determinations, and methods to synthesize panels of candidate paralogs and use of these panels to generate analyte profiles and cross reactivity matrices.

32 Claims, 23 Drawing Sheets

Positions 1–48

| # | N-term | 5 | 4 | 3 | C-term |
|---|--------|---|---|---|--------|
| 1 | V | A | V | F | A |
| 2 | F | G | W | A | I |
| 3 | G | A | V | V | F |
| 4 | V | V | I | A | P |
| 5 | A | A | A | F | F |
| 6 | M | V | V | G | W |
| 7 | I | G | G | V | A |
| 8 | G | F | W | W | M |
| 9 | S | I | P | F | I |
| 10 | W | V | G | W | A |
| 11 | G | P | G | I | F |
| 12 | A | F | V | W | S |
| 13 | N | V | W | P | W |
| 14 | W | I | G | S | W |
| 15 | G | A | G | G | F |
| 16 | G | M | W | G | W |
| 17 | F | V | A | S | G |
| 18 | W | G | A | V | P |
| 19 | A | S | M | I | A |
| 20 | V | A | V | G | S |
| 21 | V | F | S | S | V |
| 22 | M | W | V | H | W |
| 23 | S | V | A | F | P |
| 24 | S | A | M | W | W |
| 25 | A | A | V | G | H |
| 26 | F | W | W | P | H |
| 27 | A | W | S | A | W |
| 28 | W | M | V | P | S |
| 29 | P | A | G | G | W |
| 30 | W | G | S | V | S |
| 31 | V | W | W | A | A |
| 32 | S | D | W | G | M |
| 33 | S | G | W | W | G |
| 34 | M | W | H | G | P |
| 35 | W | W | S | G | S |
| 36 | W | A | P | A | G |
| 37 | A | D | W | P | S |
| 38 | W | I | S | H | W |
| 39 | G | S | A | F | H |
| 40 | A | S | G | S | S |
| 41 | S | A | A | V | A |
| 42 | G | S | S | G | S |
| 43 | W | W | W | S | G |
| 44 | A | M | M | H | W |
| 45 | N | S | S | G | G |
| 46 | W | G | G | P | M |
| 47 | P | G | P | S | G |
| 48 | G | P | H | S | A |

Positions 49–96

| # | N-term | 5 | 4 | 3 | C-term |
|---|--------|---|---|---|--------|
| 49 | G | S | S | S | F |
| 50 | G | W | G | K | W |
| 51 | W | G | D | G | P |
| 52 | N | S | W | G | A |
| 53 | S | H | P | A | W |
| 54 | S | D | A | A | A |
| 55 | A | N | H | S | A |
| 56 | D | P | W | P | W |
| 57 | W | H | G | P | H |
| 58 | S | G | D | G | V |
| 59 | H | P | H | A | M |
| 60 | S | S | H | A | G |
| 61 | G | P | K | S | A |
| 62 | H | H | G | S | W |
| 63 | A | N | S | S | W |
| 64 | S | M | D | N | W |
| 65 | A | D | A | D | A |
| 66 | G | W | S | G | A |
| 67 | N | H | P | A | G |
| 68 | M | G | K | S | H |
| 69 | N | D | M | M | W |
| 70 | A | N | K | N | G |
| 71 | G | W | S | D | D |
| 72 | G | D | P | N | G |
| 73 | H | A | A | G | D |
| 74 | S | K | S | W | G |
| 75 | D | W | S | N | K |
| 76 | A | D | H | G | G |
| 77 | G | D | S | P | D |
| 78 | S | H | D | K | P |
| 79 | P | S | H | D | M |
| 80 | S | A | G | A | K |
| 81 | D | P | N | S | D |
| 82 | M | H | D | D | P |
| 83 | P | S | D | D | N |
| 84 | D | A | S | D | H |
| 85 | H | D | D | S | S |
| 86 | G | K | M | D | K |
| 87 | D | A | K | W | D |
| 88 | S | S | H | Q | K |
| 89 | S | K | F | Q | Y |
| 90 | P | L | A | Q | G |
| 91 | P | L | A | Q | G |
| 92 | G | L | A | M | G |
| 93 | G | V | A | W | K |
| 94 | S | A | N | V | K |
| 95 | I | P | H | | D |
| 96 | F | | K | | D |

FIG. 8

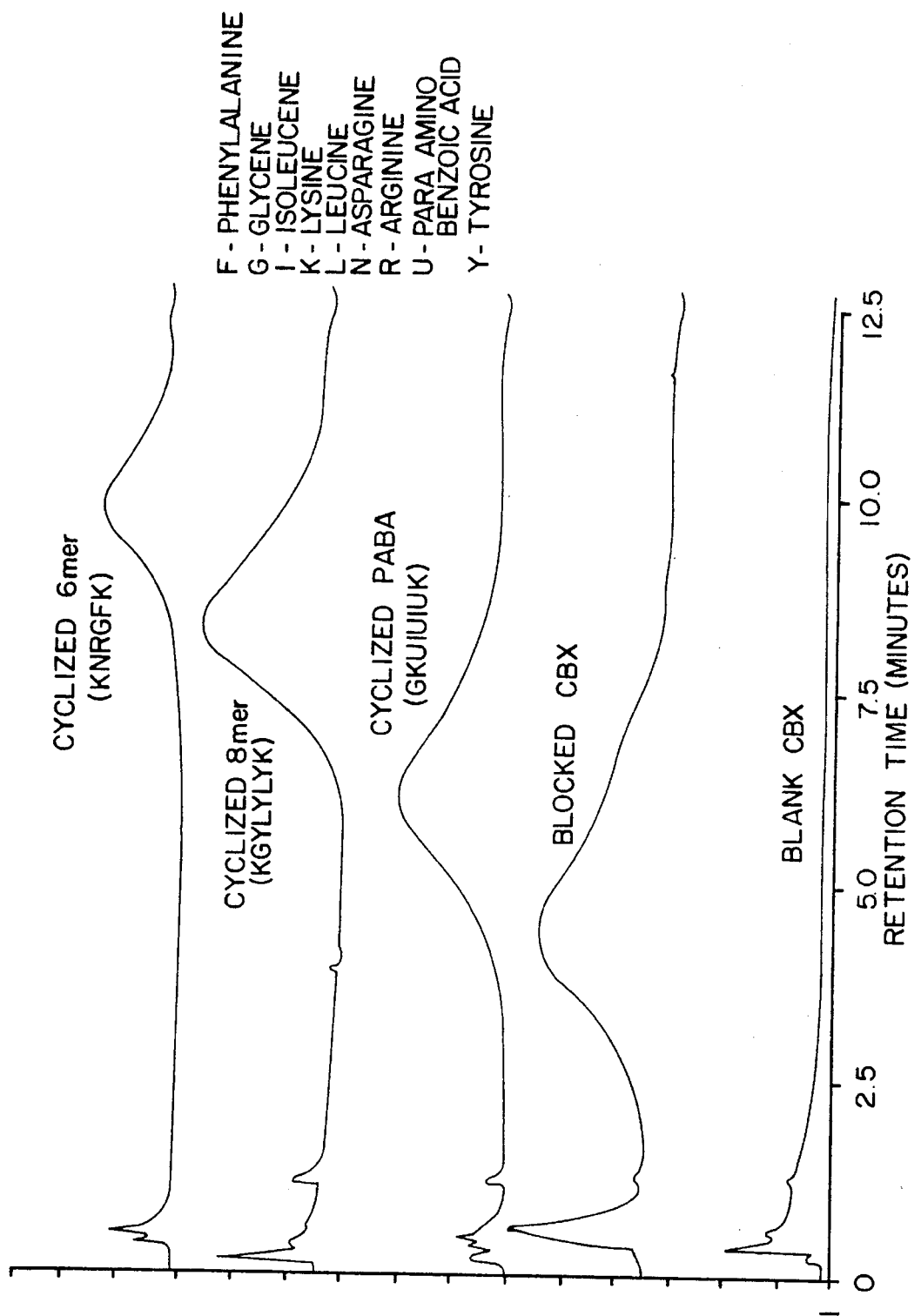

dna2 is a BASIC program written on contract for Terrapin Technologies, Inc. by Stuart Ambler 29 Sept., 1989 dna 2 output file, 10-10-1989 09:08:24
sequence seqlen   20
random number seed -4 intervals chosen by operator at run time:
   G+C percent
low  = 1        20 to 30%
high = 2        70 to 80%
   number of G+C percent regions
low  = 1         1 to  2 regions
high = 2         4 to  5 regions
   amount of direct symmetry
low  = 1         0 to  3 bases long
high = 2         5 to 10 bases long
   amount of complementary strand (dyad) symmetry
low  = 1         0 to  4 bases long
high = 2         5 to 10 bases long 16 out of 16 bins were filled in this run. Bin contents follow. The sequence is listed on the first line; the sequence with G and C replaced by 1, and A and T replaced by 0, is printed on a second line; the sequence with regions indicated by successive 1's, 2's, etc. printed on a third line; the sequence with the longest symmetry showing and other bases replaced by X is printed on a fourth line; and the sequence with the longest complementary symmetry showing and other bases replaced by X is printed on a fifth line.

```
                  per cent    # of     direct      dyad
bin description      GC      regions  symmetry   symmetry
................................................................
bin number            1         1         1         1
bin properties       30         2         3         0

GATTATTACTTTGGATGTAG
10000000100011001001
11111111111122222222
xATTxTTAxxxxxxxxxxxx
xxxxxxxxxxxxxxxxxxxx ................................................................
bin number            1         1         1         2
bin properties       25         2         3         8

TAAGTTATCTATAACTTAGG
00010000100000100011
11111111111111112222
xxxxxTATxTATxxxxxxxx
TAAGTTATxxATAACTTAxx
```

FIG. IIA

|  | bin description | per cent GC | # of regions | direct symmetry | dyad symmetry |
|---|---|---|---|---|---|

```
bin number              1     1     2     1
bin properties         20     2     5     0

ATAGGATTTAAGTAATTTTG
00011000000100000001
11111222222222222222
xxxxxxTTTAAxxAATTTxx
xxxxxxxxxxxxxxxxxxxx bin number              1     1     2     2
bin properties         30     1     5     5

CAATGATTGTAACATTGAGA
10001000100010001010
11111111111111111111
CAATGxxxGTAACxxxxxxx
CAATGxxxxxxxCATTGxxx bin number              1     2     1     1
bin properties         30     4     0     0

ATCATTCAGGTATACTTGTA
00100010110000100100
11111122223333444444
xxxxxxxxxxxxxxxxxxxx
xxxxxxxxxxxxxxxxxxxx bin number              1     2     1     2
bin properties         25     4     3     5

ATACCTAAATAGACGATTTA
00011000000101100000
11111222223333344444
xxxxxxxxxTAGxxGATxxx
xxxxxTAAATxxxxxATTTA bin number              1     2     2     1
bin properties         30     4     5     0

ATTCAACTACTAATCATTCC
00010010010000100011
11111122223333334444
xxxxxxxTACTAATCATxxx
xxxxxxxxxxxxxxxxxxxx
```

FIG. 11B

| bin description | per cent GC | # of regions | direct symmetry | dyad symmetry |
|---|---|---|---|---|
| bin number | 1 | 2 | 2 | 2 |
| bin properties | 25 | 4 | 5 | 6 |

```
AAAATCAGGATTTTAGGTAT
00000101100000011000
11111222233333344444
xxxxxxxGGATTTTAGGxxx
AAAATCxxGATTTTxxxxxx
```

| bin description | per cent GC | # of regions | direct symmetry | dyad symmetry |
|---|---|---|---|---|
| bin number | 2 | 1 | 1 | 1 |
| bin properties | 70 | 2 | 3 | 0 |

```
TTCACGGTGGCGCAGGCCCT
00101110111110111110
11112222222222222222
xxxxCGGxGGCxxxxxxxxx
xxxxxxxxxxxxxxxxxxxx
```

| bin description | per cent GC | # of regions | direct symmetry | dyad symmetry |
|---|---|---|---|---|
| bin number | 2 | 1 | 1 | 2 |
| bin properties | 80 | 2 | 3 | 5 |

```
ACCCCGGGGCTAGCCCCTCG
01111111110011111011
11111111112222222222
xxxxCGGGGCxxxxxxxxxx
xxxxxGGGGCxxGCCCCxxx
```

| bin description | per cent GC | # of regions | direct symmetry | dyad symmetry |
|---|---|---|---|---|
| bin number | 2 | 1 | 2 | 1 |
| bin properties | 80 | 2 | 5 | 0 |

```
TCCACCCTGCCGGCCCCGTC
01101110111111111101
11111111222222222222
xxxxxxCTGCCxxxxCCGTC
xxxxxxxxxxxxxxxxxxxx
```

| bin description | per cent GC | # of regions | direct symmetry | dyad symmetry |
|---|---|---|---|---|
| bin number | 2 | 1 | 2 | 2 |
| bin properties | 80 | 2 | 5 | 5 |

```
CCGGTCCCGTGGCCGGACCA
11110111101111110110
11111111111111112222
CCGGTxxxxTGGCCxxxxxx
xxGGTCCxxxxxxxxGGACCx
```

FIG. IIC

| bin description | per cent GC | # of regions | direct symmetry | dyad symmetry |
|---|---|---|---|---|
| bin number | 2 | 2 | 1 | 1 |
| bin properties | 70 | 4 | 3 | 0 |

```
TCCTGCCTCGGCACTTCCCG
01101110111101001111
11111111222233334444
TCCxxCCTxxxxxxxxxxxx
xxxxxxxxxxxxxxxxxxxx
```

| bin number | 2 | 2 | 1 | 2 |
|---|---|---|---|---|
| bin properties | 70 | 5 | 2 | 5 |

```
CCGGAACGCGCGATATCCGG
11110011111100001111
11112222333344445555
xxxxxxCGxGCxxxxxxxxx
CCGGAxxxxxxxxxxTCCGG
```

| bin number | 2 | 2 | 2 | 1 |
|---|---|---|---|---|
| bin properties | 75 | 4 | 5 | 0 |

```
AGAGTGCGGGTCAGGGCGGG
01010111110101111111
11112222233334444444
xxxxxGCGGGxxxGGGCGxx
xxxxxxxxxxxxxxxxxxxx
```

| bin number | 2 | 2 | 2 | 2 |
|---|---|---|---|---|
| bin properties | 70 | 4 | 5 | 5 |

```
ACTGGCGCACAACGCGCCCT
01011111010011111110
11122223333444444444
xxxxGCGCAxxACGCGxxxx
xxxGGCGCxxxxxGCGCCxx
```

FIG. 11D

METHOD TO IDENTIFY ANALYTE-BINDING LIGANDS

CROSS-REFERENCE TO RELATED APPLICATION

This application is a division of application Ser. No. 08/116,059, filed Sep. 2, 1993, now U.S. Pat. No. 5,409,611, which, in turn, is a division of application Ser. No. 08/049, 642, filed Apr. 9, 1993, now U.S. Pat. No. 5, 340,474, which, in turn, is a continuation-in-part of U.S. Ser. No. 429,721 filed 31 Oct. 1989, now U.S. Pat. No. 5,133,866, which is a continuation-in-part of U.S. Ser. No. 355,042, filed 16 May 1989, now U.S. Pat. No. 4,963,263, which is a file wrapper continuation of U.S. Ser. No. 172,626, filed 24 Mar. 1988, now abandoned, and is also a continuation-in-part of U.S. Ser. No. 255,906, filed 11 Oct. 1988.

TECHNICAL FIELD

The invention relates to selection of specific binding moieties which can, for example, be used as chromatographic and analytical affinity ligands for specific analytes. More particularly, it concerns use of ligands selected from diverse sets of low molecular weight (<7.5 kd) "paralogs" of varying properties as affinity ligands which are useful in diagnosis and therapy, and in chromatographic techniques for detection and purification of a variety of analytes, in particular toxic contaminants of low immunogenicity, and in binding assays, such as immunoassays.

BACKGROUND ART

The paralogs prepared by the method of the invention are particularly useful in chromatographic applications. Two major developments in the practice of such chromatographic separations have been of dramatic importance over the last decade or so in facilitating the isolation of natural products, separation of components of mixtures, and analysis of complex compositions. These are the proliferation of the variety of available ligands such as specific antibodies for affinity chromatography, wherein the separation or analysis depends on a large difference in binding properties resulting from the specific interaction between a supported ligand and a desired analyte, and the advent of high performance liquid chromatography (HPLC) which permits rapid and efficient separation of multiple components through repetitive partitioning depending on small differences in their binding to a sorbent. These developments have overlapped only to a limited extent, as HPLC generally utilizes conditions which are inimical to many of the ligands used as specific affinity partners. The most common affinity partner for use in these techniques with respect to a spectrum of possible analytes has been a specific immunoglobulin or an immunoreactive fragment thereof. In general, this type of ligand is unstable with respect to the conditions employed in HPLC. HPLC often employs nonaqueous solvents, which are denaturing to many affinity ligands and the high pressures employed are also destructive to many of these substances.

In affinity based chromatography, a variety of solid supports and of affinity ligands can be used, as summarized in an early review article by May, S. W., in *Separation and Purification* 3rd Ed. (1978) Edmond S. Perry, et al., ed., vol. 12 in *Techniques of Chemistry* (J. Wiley). This review describes suitable supports for affinity chromatography emphasizing polysaccharide supports in addition to polyacrylamide gels, mixed gels, and various glasses and silica derivatives. Of these, only silica derivatives have gained wide acceptance for use in HPLC. However, the extent of derivatization of the support to modify its binding characteristics has been limited to altering hydrophobicity by conjugation of various hydrocarbon ligands or other simple molecules.

The present invention enables a convenient crossover between the HPLC and affinity approaches by providing a method to obtain ligands which have the required affinity specific for a selected member of an array of possible analytes as well as capability to withstand the conditions of HPLC. By providing maximal diversity in the choice of these ligands, there is made available an appropriate ligand to effect the desired separation in any arbitrary instance.

Others have attempted the crossover between HPLC and affinity chromatography in various ways. Peterson, E. A., et al., *Meth Enz* (1984) 104:113–133, describe "displacement" chromatography wherein competition for the adsorption sites between adsorbed components is substituted for competition with eluant. Chromatographic supports which employ carbohydrates, such as cyclodextrins, with differential specific affinities for the substances to be separated have also been reported (Armstrong, D. W., et al., *J Chrom Sci* (1984) 22:411–415). In addition, panels of purified Cibacron dyes have been used as candidate chromatographic supports (Burton, S. J., et al., *J Chromatog* (1988) 435:127–137).

An example of the ligands employed in the invention method are diverse sets of peptides of 4–20 amino acids, which are one form of the materials designated "paralogs" herein. A paralog mimics the portion of an immunoglobulin which specifically binds to the antigenic determinant or epitope of the antigen to which the antibody is raised. The segment complementary to this epitope is commonly designated a paratope, and since a peptide sequence in the paralog need not be the same as that occurring in the raised antibodies, the term paralog (or paratope analog) is used.

Synthesis of, and identification of, peptides which putatively are complementary to specific moieties has been done previously to a very limited extent. Atassi, M. Z., et al., *J Biol Chem* (1977) 252:8784–8787, described the specific design of a peptide complementary to the antigenic sites of lysozyme. Knowledge of the three-dimensional contours of lysozyme permitted the synthesis of a peptide of dimensions and electron density patterns analogous to the deduced determinant. The putatively complementary peptide was obtained by preparing a sequence deliberately complementary in dimension and electron distribution to the determinant-mimicking peptide. The pseudo "paratope" peptides inhibited the reaction of lysozyme with antisera and specifically bound lysozyme to the exclusion of myoglobin or antibody. However, this property was later shown to be shared, and, in fact, exceeded by the peptide to which this "paratope" was a complement. Later work from the same group resulted in the synthesis of a peptide representing the acetyl choline binding site of a specific receptor and of a binding site in trypsin (McCormick, D. J., et al., *Biochem J* (1984) 224:995–1000; Atassi, M. Z., *Biochem J* (1985) 226:477–485). The paratope or receptor or enzyme binding site-mimicking peptides were based on known structural parameters associated either with the antigenic determinant or with the determinant binding moiety.

In a different approach to defining binding sites at atomic resolution, recent work has shown that the idiotypic surface of antibodies can be mapped and peptides mimicking portions of this surface can be prepared. Contrary to expectation from Jerne's hypothesis, however, the idiotopes and paratopes do not precisely coincide. Seiden, M. V., *Am Assoc*

*Immunol* (1986) 136:582–587; Roux, K. H., et al., *Proc Natl Acad Sci USA* (1987) 84:4984–4988.

Recently, methods to mimic epitopes as specifically binding complementary components without knowledge of the characteristics of the specific interaction have been disclosed. The most relevant work is that of Geysen, H. M. at the Commonwealth Serum Laboratories in Australia. Geysen has devised an empirical method for preparing a panel of multiple candidate sequences whose ability to bind specifically to antibody can be empirically tested. In the Geysen approach, each of the candidate peptides is separately synthesized on an individual polyethylene support rod in relatively small amount. The support rods are arranged conveniently so as to dip individually into the wells of a microtiter tray. Typically 96 separate peptides can be simultaneously synthesized (the number corresponding to the arrangement of commercially available trays). The 96 peptides can also be simultaneously assayed for binding to antibodies or receptors using standard radioimmunoassay or ELISA techniques. (See, for example, *Proc Natl Acad Sci* (USA) (1984) 81:3998–4002, PCT applications WO86/00991 and WO86/06487.)

A variety of candidate peptides can also be simultaneously synthesized in separate containers using the T-bag method of Houghten, R., *Proc Natl Acad Sci* (USA) (1985) 82:5131–5135.

If the repertoire of gene-encoded amino acids is satisfactory, the candidate peptides can be prepared recombinantly from randomly generated DNA sequences as described in our earlier application, published as WO 89/03430, published 20 Apr. 1989 (see p. 34). Specific embodiments of this approach were recently published Devlin, J., et al. *Science* (1990)249:404–405; Scott, J. K., ibid, pp. 386–390.

The general basis for paralog-based chromatography has been described by applicant (Kauvar, L., et al., *BioTechniques* (1990) 8:204–207). Methods are also available for synthesis of alternate, nonpeptide, forms of candidate paralogs in multiple diverse sets. Thus, any moiety which is a composite molecule synthesized from a multiplicity of monomer units with varying properties, which monomer units can be varied across the members of a panel, can form the basis for the set of candidate paralogs.

These and other elements of the synthetic art can be productively used as a resource to construct the ligands needed for the conduct of the methods of the herein invention, and for uses such as for the preparation of chromatographic substrates or other specific binding applications.

DISCLOSURE OF THE INVENTION

The invention makes possible the systematic and facile selection of a substance capable of specific binding to any selected moiety. In one application, the invention provides a useful form of analytical and preparative chromatography on solid supports which permits a combination of the advantages of affinity chromatography and HPLC. By selecting and constructing appropriate substrates for chromatographic separations and purifications based on affinity, these procedures can be carried out under efficient conditions which permit ready analysis of components, or their purification or their removal from mixtures. Such techniques are particularly useful in removing toxic wastes from effluents, in assaying the quantity of toxins in reservoirs, in analysis of levels of materials at low concentration in the presence of a high concentration of irrelevant contaminants, and in preparative procedures involving HPLC. The invention permits this efficient use of chromatographic techniques by using effective means to ascertain appropriate paralog ligands for particular purification and separation problems, or for a desired binding assay. Moreover, the invention method can provide a specifically binding paralog useful in a variety of contexts, including diagnosis and therapy. In addition, the availability of the diverse paralog panels of the invention permits the construction of binding profile characteristic of any arbitrary analyte as well as permitting the systematic study of molecular interactions—in particular, peptide/peptide interactions—by providing informative interaction matrices.

Thus, in one aspect, the invention is directed to methods to obtain paralogs having specific affinity for a specified moiety, such as an analyte. The method of the invention comprises screening, for ability to selectively bind said moiety, a panel of individual candidate paralogs wherein said candidate paralogs have systematically varied values of at least two parameters which determine the ability of the paralog to bind other substances. In addition, the candidate paralogs may contain substituents that are specific for the predetermined moiety. The substituent will exhibit this specificity in graded amount depending on the remainder of the paralog structure. Systematic variation in properties greatly reduces the number of candidates that need to be screened thus providing a significant advance over prior methods.

The invention further provides means to obtain increasingly good approximation to a maximally diverse set, thus further reducing the number of candidates that need to be screened. Such screening may be done by individually testing each member of the panel with the moiety to be bound, or by means of kits which provide multiple test portions for simultaneous screening of panel candidates.

The candidate paralogs can be prepared by synthesizing the polymeric composite paralog moieties from monomer components in a manner predetermined to maximize the diversity of the parameters or may be prepared by synthesizing a random mixture of such paralogs and isolating diverse candidates by binding to and elution from an approximately maximally diverse set of complementary ligands. Alternatively, statistical analysis of empirically derived cross-recognition tables can be used to identify the maximally diverse set.

In other aspects, the invention is directed to the paralog panels per se, to kits suitable for screening the paralog panels, and to analyte profiles and interaction matrices determined by reaction of panels with analyte or cross-reaction of the panels. The invention, in other aspects, is directed to gradient chromatographic supports prepared from at least a portion of the paralogs of the panels and to separation methods using these supports.

As mentioned above, in addition to chromatographic applications, the individual paralogs of correct specificity can be used as substitutes for antibodies or fragments thereof in immunoassay procedures. The paralogs may also be used instead of antibodies to screen mimotope panels for members capable of substituting for a particular hapten in the method of pseudo-idiotypic network (PIN) profiling described in the above-cited PCT publication WO89/03430, published 20 Apr. 1989. The specifically binding paralogs are also useful in contexts wherein the moiety to be bound is a receptor, such as in therapy.

BRIEF DESCRIPTION OF THE DRAWINGS

FIG. 8 shows the panel of 90 candidate pentapeptide paralogs synthesized according to Example 1.

FIG. 10 shows the effect of cyclization of peptides on their behavior as chromatographic substrates for DDD.

FIGS. 11-1, 11A, 11B, 11C, and 11D show a panel of diverse DNA sequences designed by computer.

MODES OF CARRYING OUT THE INVENTION

Figure 1:
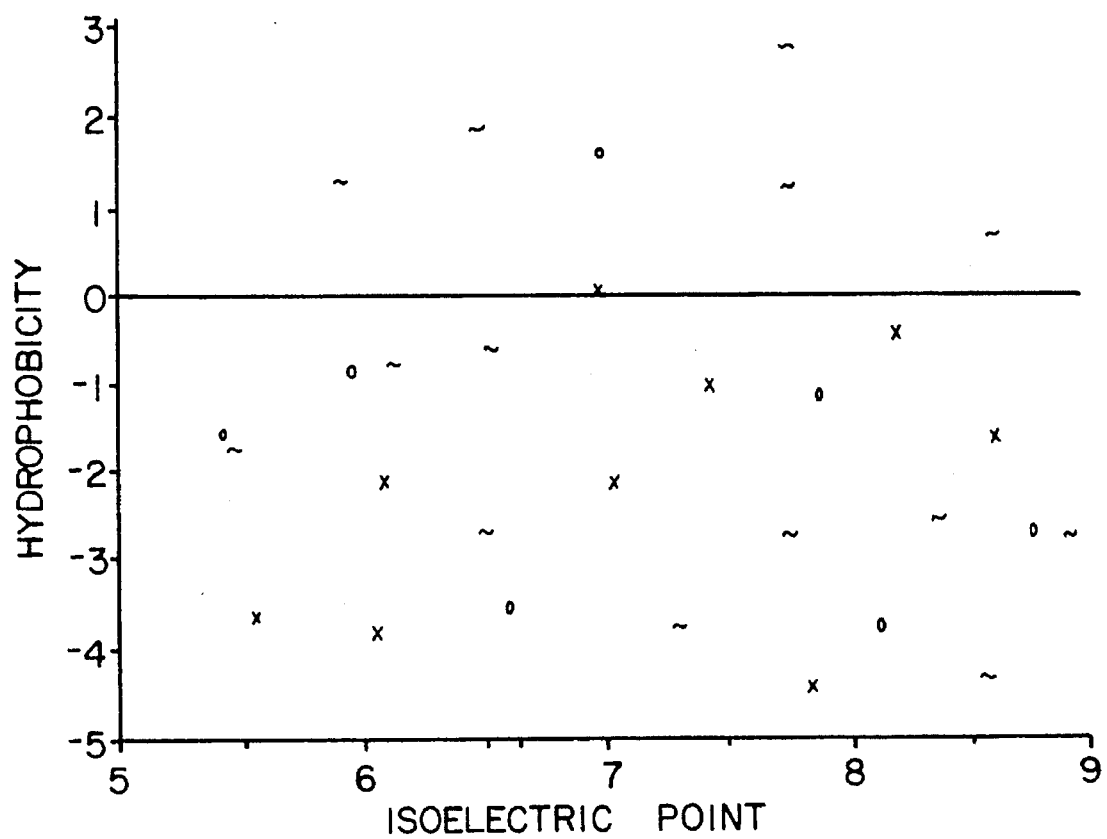
FIG. 1 shows the characteristics of a diverse set of 30 peptides generated by a FORTRAN program.

As used herein, "paralog" refers to a short "polymer" of MW <7500, or preferably <5000, more preferably <1000, composed of monomer units, which polymer has specific affinity for a specified moiety, such as an analyte or hapten. This "polymer" responsible for the affinity may, of course, be included in a larger molecule or conjugated to a solid support, and may be supplied as tandem copies. Advantage may also be taken of coupling to phage coat protein as referenced above.

For selection by the screening method of the invention, an individual paralog is originally synthesized as a member of a panel of candidate paralogs which have maximized diversity with respect to at least two parameters which affect the ability of the paralog to bind to another substance. Therefore, the paralogs of the invention must be, in order to permit rational synthesis of the panel, composed of individual monomer units which monomer units can be varied across the members of the panel in a combinatorial fashion, thus generating the necessary superabundant diversity in a preparation. The diversity can be obtained by systematic variation of parameters through the design of synthesis of individual panel members, or may be achieved by the synthesis of random mixtures, depending on the approach to the formulation of the panel.

"Maximal" diversity refers to variation of a property among the candidates over a range that is reasonably wide. The width of range required may vary depending on intended use and, of course, the outer limits of a theoretical range are not necessarily reached per se, but can be approached to any desired closeness.

The resultant paralogs are "polymers", but need not be, and indeed cannot be, homopolymers such as polyethylene or polypropylene, and need not even be pseudohomopolymers—i.e., composed of monomeric units where the same type of linkage is employed to conjugate the monomeric units, such as is the case for peptides or nucleic acids, where individual monomers may vary but the basic linkage remains the same. A wide variety of such composite polymeric molecules may be used as members of the paralog panel of the invention, as will further be described below, but all share the characteristic of permitting synthesis of vastly more candidates than can be practically screened, thus creating a need for systematic methods of design and preparation of a diverse subset as provided by the invention.

The nature of the advantage of moieties composed of monomer units is seen, for example, in the case of peptides. If paralogs containing 6 amino acids in their primary sequence are employed, there are 64 million possible 6-mers using only the 20 naturally occurring amino acids. Of course, the synthesis of peptides need not be limited to these naturally occurring subunits, and the D-forms of the encoded amino acids as well as various nonencoded amino acids such as beta alanine, amino-butyric acid, citrulline, and the like can also be used. Hundreds of such non-encoded amino acids are known. Indeed, these may be preferred as they are expected to be more stable than the "natural" amino acids which are metabolites for microorganisms.

Paralogs provide spatial conformation and electron distribution patterns which are comparable in diversity to that generated by the immune system. While the paralog can be conceptualized in this manner as an antibody mimic it is, of course, not necessary that administration of the moiety intended to be bound by the paralog, in fact, in every instance (or in any instance) raise immunoglobulins with a paratope of precisely the conformation and pattern of the paralog. It is sufficient that the paralog is capable of exhibiting analogous specific affinity properties with respect to the selected moiety.

"Specific affinity" refers to the ability of the paralog to bind to the selected moiety specifically—i.e., the strength of the interaction between this moiety and paralog is effectively greater than the strength of the interaction between the paralog and other materials which might be present with the selected moiety, so that binding to the paralog can be used to distinguish between for example, an analyte and a contaminant. Typical values for the specific affinity are of the order of $10^3$ l/mole to $10^4$ l/mole at a minimum, and are preferably $10^8$ or $10^{10}$ l/mole. The needed value is dependent on the environment in which the selected moiety is found, and on the relative binding strength of the accompanying materials as well as their concentration. In some contexts, a lower affinity is quite adequate, or even preferable, for subsequent ease in elution, whereas if the paralog also binds strongly to the accompanying materials, especially those present in high concentration, a higher affinity may be required in order to set the binding of the selected moiety apart from that of these materials. In short, it is the relative affinity for the selected moiety in comparison with that for accompanying materials that is critical. However, the specific affinity should preferably result from the combined charge/spatial array characteristic of the paralog as complementary to the selected moiety, rather than entirely from a single generalized property such as pI or hydrophobic index.

The term "substituent specifically binding to" a target substance or substrate has a slightly different meaning from "specific affinity" above. This refers to the ability of the substituent to retrieve a class of substances, although not necessarily, and preferably not, distinguishing between members of the class. Thus, examples of substituents specifically binding to subsets of substances include boronate residues which bind specifically to carbohydrates and/or glycoproteins; cofactors which bind selectively to a class of enzyme utilizing said cofactors; and analogs of substrates for enzymes which bind selectively to those enzymes which utilize the substrate. In general, the substituents specifically binding to a class of substances are employed to effect a simultaneous gross separation of the desired substances from crude mixtures while using the systematically varied parameters of the paralog panel to discriminate among the members of the class. The ability of the substituent itself to bind the target moiety will also be affected by the structure of the paralog in which it resides; thus the paralogs containing said substituent discriminate among members of a class of target moieties both by virtue of the inherent variation in the paralog and by virtue of variation in the strength of attraction by the substituent in these varied environments.

Assessment of binding affinity of the target moiety for a paralog can be made taking advantage of standard immunological methods. Methods to measure the affinity of interaction between antigens and high-affinity antibodies is standard; that of interaction with low-affinity antibodies can be measured as described, for example, Takeo, K., et al., *J Immunol* (1978) 121:2305–2310. Takeo et al describe measurement of binding constants of certain oligosaccharides to specific myeloma proteins using polyacrylamide gel electrophoresis and varying the nature and content of the oligosaccharides in the gel when determining mobilities of the proteins. The method is said to be useful in obtaining binding constants ranging from $10^2$–$10^6$ liters per mole. Varga, J. M., et al., *J Immunol* (1974) 112:1565–1570, describe the determination of binding constants across a comparable range using nylon-polystyrene whisker discs coupled by glutaraldehyde to immunoglobulins to test the binding of radioactive ligands. Thus, there are a number of protocols in addition to the currently used standard dilution immunoassay procedures in microtiter wells to evaluate binding and quantitate binding constants.

The invention provides means to screen panels to obtain paralogs which have specific affinity for a wide variety of selected moieties which may or may not be immunogenic. In addition to moieties which are themselves peptides, and which therefore may permit direct design of individual paralogs by the "complementarity" approach with regard to sequential overlapping portions of the primary amino acid sequence (a combination of the synthesis/analysis method of Geysen with the complementarity design approach of Atassi) the moieties to be bound may be of any origin including drugs such as penicillin, tetracycline, steroids, naproxen, theophylline, vitamins, such as vitamins K, D and A, various toxins such as PCBs, dioxin, and tetrabromoethylene, and any miscellaneous chemical substance having a defined molecular conformation or shape under specified conditions. Using the method of the invention, a specific peptide paralog can be found for virtually any type of moiety or a defined region thereof.

As stated above, the paralog panels may also be provided with specific binding substituents which remove a class of moieties to be determined while providing, among the paralog panel itself, means to discriminate between individual members of a class. In one application of this approach, boronate substituents, such as those disclosed in U.S. Pat. No. 4,499,082 to Du Pont, can be used to bind selectively carbohydrate-containing materials such as carbohydrates per se and glycoproteins, including those glycoproteins found on cellular surfaces. Boronates immobilized to columns have been reported for the separation of glycose-containing molecules by, for example, Mazzio, J. R. et al., *BioChromatography* (1989) 4:124–130. The boronate residue is thought to react specifically with the cis diols contained in sugar residues. Boronate affinity columns have also been used to separate normal and non-glycosylated hemoglobin by Klenk, D. C. et al. *Clin Chem* (1982) 22:2088–2094. The boronate residue can readily be included in the paralog panel, for example, by utilizing the α-amino boronate-derivatized peptide acids described in the above-referenced patent. These compounds are peptides having an amide residue at the C-terminus which is derivatized to a residue of the formula $R-CHB(OH)_2$. This patent further references prior art boronates which contain the residue $CH_2B(OH)_2$ attached to an oxygen atom rather than nitrogen.

Also useful in the present invention are peptides synthesized from amino acids which contain boronate residues in their side chains, rather than as substituents on C-terminal amide. With derivatization to the side chain the modified amino acids can be employed routinely in standard solid-phase (or solution-phase) peptide synthesis. The inclusion of the specific binding substituent then permits application of the method of the invention to discriminate among members of a group by virtue of differential binding across the class thereby enabling systematic retrieval of the group to which the differential binding is to be applied.

The utilization of boronate is analogous to use of other carbohydrate-binding moieties such as lectins as the specific binding substituent. This has particular advantage in cell separation techniques, as most cells are characterized by surface glycoproteins. The inclusion of the specific binding substituent then enables removal of cells from crude mixtures containing other components such as proteins, fats, etc., and subsequent discrimination among the harvested cells using the differential properties of the paralog panel. The differential properties of the paralog panel with respect to the various glycoprotein containing cells results both from the variation in accessibility of the specific binding substituent to the target glycose residues and from the inherent diversity of the panel. Other applications of this general approach include varying accessibility to cofactors or substrate analogs to retrieve classes of enzymes, such as the use of substrate analogs to differentiate among zinc-ion dependent metalloproteinases.

The obtention of the paralog for selected moieties, whether peptides or nonpeptides, can be approached by a screening procedure among candidate paralog peptides. In this approach, a panel of candidate paralogs having maximally diverse values for at least two parameters related to ability to bind other substances is prepared for screening. The panel is thus designed to cover a wide range of electron cloud pattern alternatives so that an approximation of the desired paralog can be obtained. Subsequent candidates within that range can be further tested for fine tuning.

In order to cover the range of electron cloud patterns which determine, it is understood, the ability of the paralog to bind to other substances, at least two parameters must be varied over more or less a maximal range. By "variation over a maximal range" is meant that the parameter has values which cover the useful range of values ordinarily found for this parameter, which range may be dependent on the context. For example, the isoelectric point, pI, ordinarily would vary over a range of about 2–12; theoretical values beyond these limits can certainly be postulated, but as a practical matter there is little point in attempting to reach, for example, pH 0. It will be apparent to one of ordinary skill in the art what sort of maximal variation is useful. Indeed, panels having useful variation in the values of single parameters already exist—chromatographic supports are available, for example, in a range of hydrophobicities and ion exchange columns are available in a range of charge densities.

The identification of at least two parameters which can be varied widely in order to assure a wide range of binding affinities for the panel will depend on the chemical nature of the candidate paralogs in the panel, as will be further described below. While such parameters as hydrophobic moment and corrugation factor can readily be calculated for candidate peptides, panels of nucleic acids, for example, may vary in the number and spacing of homopolymeric regions and in symmetry indices. Derivatized polysaccharides may vary in branching and charge distribution. In all cases, the candidate panel is made up of individual paralogs which are maximally diverse over at least two such parameters, thus leading to a set with superabundant diversity. This is in contrast to prior art approaches where either only one parameter is varied (as is the case with supports for chromatography which vary only in hydrophobicity, or is the case of ampholyte supports which vary only in pI) or which have undefined variabilities over a very small range (such as is the case for the cyclodextrin based chromatographic supports or for affinity matrices based on textile dyes).

For example, there are commercially available kits marketed by ICN for empirical choice of chromatographic supports useful in protein separation which are based on a series of affinity ligands representing analogs of Cibacron dyes. These dyes, which are non polymeric, vary in properties only over a very narrow range. Because of the non-polymeric nature of the dyes, systematic variation of the nature of the components does not provide the opportunity to obtain such a wide range of values among the members of the panel. The invention panels, in contrast, provide a range of diversity over an electron configuration and charge contour map as defined by at least two specific parameters. As is further described below, the variation in invention panels can be achieved in three general ways: by the design of the panel based on systematic variation of two or more parameters; by screening a randomly generated panel against a complementary, maximally diverse, counter-panel which had been achieved through systematic two parameter variation design; or by statistical analysis of iterative screening of random panels against each other. This last alternative, a "boot strap" method which results from sorting the members of two random panels on the basis of their cross reactivity is further described in PCT application WO 89/03430 referenced above. The superior result of the capability to provide maximal variation is shown by a comparison of the dye-based panels with those of the invention set forth in Example 6 below.

One set of polymers which is extremely convenient from the standpoint of synthesis is comprised of peptides since the nature of amino acyl residues, both naturally-occurring encoded residues, and others, provides a range of properties which is very easily incorporated in a systematic manner into the synthesis of a group of polymeric sequences. Such peptides can, of course, be modified to vary the nature of the linkage so that they may be considered "pseudopeptides" by converting the amide linkages to alternate forms using generally recognized means. Specifically, the peptide linkages can be replaced with other types of linkages such as —$CH_2NH$—, —$CH_2S$—, —$CH_2CH_2$—, —$CH=CH$— (cis and trans), —$COCH_2$—, —$CH(OH)CH_2$—, and —$CH_2SO$—, by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F., in "Chemistry and Biochemistry of Amino Acids Peptides and Proteins" B. Weinstein, eds, Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—$CH_2NHY$—, —$CH_2CH_2$—); Spatola A. F. et al., *Life Sci* (1986) 38:1243–1249 (—$CH_2$—S); Hann, M. M., *J Chem Soc Perkin Trans I* (1982) 307–314 (—CH—CH—, cis and trans); Almquist, R. G., et al., *J Med Chem* (1980) 23:1392–1398 (—$COCH_2$—); Jennings-White, C., et al., *Tetrahedron Lett* (1982) 23:2533 (—$COCH_2$—); Szelke, M., et al., European Appln EP 45665 (1982) CA: 97:39405 (1982) (—$CH(OH)CH_2$—); Holladay, M. W., et al., *Tetrahedron Lett* (1983) 24.:4401–4404 (—$CH(OH)CH_2$—); and Hruby, V. J., *Life Sci* (1982) 31 189–199 (—$CH_2$—S—). Particularly preferred is —$CH_2NH$—.

The peptides themselves can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc-protected C-terminal residues can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart, et al., *Solid-Phase Peptide Synthesis* (1969) W. H. Freeman Co., San Francisco and Merrifield, *J Am Chem Soc* (1963) 85:2149–2154. These and other methods of peptide synthesis are also exemplified by U.S. Pat. Nos. 3,862,925, 3,842,067, 3,972,859, and 4,105,602.

The synthesis may use manual techniques or automatically employ, for example, an Applied BioSystems 430A Peptide Synthesizer (Foster City, Calif.) or a Biosearch SAM II automatic peptide synthesizer (Biosearch, Inc. San Rafael, Calif.), following the instructions provided in the instruction manual supplied by the manufacturer.

Alternatively, peptide paralogs can be produced by expression of recombinant DNA constructs prepared in accordance with well-known methods. Such production can be desirable to provide large quantities and, by using mixtures of encoding DNAs, multiple embodiments of the paralogs can be obtained. While large members of candidates are produced, the mixture is only random. Since the peptide sequences are relatively short, however, recombinant production is facilitated. While completely randomized DNA sequences can be used for the preparation of the paralogs, the process can be made more efficient by randomizing triplets rather than individual nucleotide bases. In addition, recombinant production can be used to produce specifically designed paralogs. Of course, these paralogs are limited to those which are constructed of amino acids which are encoded in the gene, or which can be readily be formed from such amino acids.

Cyclic forms of the peptides can also be obtained using generally known methods. For chromatographic applications, it is advantageous to attach the linear compound to the solid support before conducting the cyclization reaction to promote intramolecular (as opposed to intermolecular) bonding. Disulfide linkages are formed by reacting peptides containing cysteine or cysteine analog residues with reagents which result in the formation of disulfide bonds, such as, for example, mildly oxidizing conditions. Esters and amides involving the sidechains of amino acids can be obtained synthetically by a suitable protection/deprotection protocol. It is understood that the requirements for deprotection vary with the protecting group; F-moc is released by the organic base piperidine, however, sidechain protecting groups are generally protected with groups which are stable to base, but labile to dilute trifluoroacetic acid (TFA). Another commonly used protecting group t-Boc is released by TFA, but alternative sidechain protecting groups can be used which are labile only to stronger conditions of treatment, with hydrogen fluoride, for example. Thus, the protecting agents can be removed from the groups whose interaction forms the backbone chain while sidechain carboxyl, amino, and hydroxyl groups such as the amino group of lysine, the carboxyl of aspartic acid, and the hydroxyl of threonine are protected by groups stable to the deprotection involved in the peptide synthesis. After the peptide is synthesized, deprotection of these groups in amino acids spaced 3–4 residues apart in the peptide chain, for example, followed by treatment with a standard peptide bond forming reagent such as dicyclohexylcarbodiimide (DCC) results in an internal loop of these 3–4 amino acids. Cyclic forms of the peptides which mimic paratopes or which otherwise exhibit specific binding may also be obtained by controlling the 3-dimensional conformation through the use of "molecular sticks" as described in applicant's PCT application WO 89/90233 published 10 May 1989. Also, crosslinking may be effected using homo- or hetero-bifunctional linkers such as those available from Pierce Chemical Co., Rockford, Ill.

In an additional modification of peptide paralogs, the individual amino acid residues may be separated by peptide-like moieties which introduce conformational restraints. For example, "amino acyl" monomers of the formulas

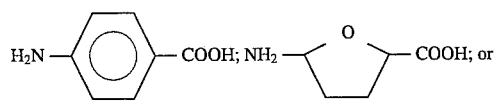

-continued

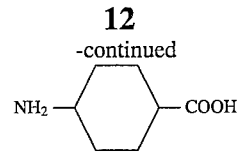

can be used between "normal" amino acyl residues in the synthesis of the peptides.

The choice of parameters for which maximal variation is to be obtained depends upon the nature of the paralog. For paralogs which are peptides, or compounds related to peptides such as peptides with altered linkages and/or their cyclized forms described above, at least seven such parameters are useful candidates for variation. Two of these parameters are largely independent of conformation—the hydrophobic index and isoelectric point. Five of them are conformation-dependent and include the hydrophobic moment (a measure of the amphipathicity of the peptide or the extent of asymmetry in the distribution of polar and nonpolar residues); the lateral dipole moment, a measure of asymmetry in the distribution of charge); a corrugation factor (defined by the inventors herein, which measures the variation in surface contour—for example, the scatter and the distribution of bulky sidechains along the helical backbone); aromaticity (which is a measure of pi-pi interaction among aromatic residues included in the paralog); and the linear distance between charged atoms. These parameters will be discussed in turn.

The isoelectric point, pI, has its conventional meaning and, as is well known, refers to the pH at which the molecule referred to is electrically neutral. The pI can be altered to higher values by increasing the number of basic amino acids, such as lysine, arginine or histidine, which are positively charged at neutral pH. The pI can be shifted toward lower values by increasing the relative numbers of acidic amino acid such as aspartic acid or glutamic acid which are negatively charged at neutral pH. Intermediate pI values can be achieved by balancing the positive and negatively charged groups or by using uncharged amino acyl residues. Although gene-encoded amino acids have been used for ease of reference it is, of course, understood that any suitable amino acyl residue can be used, whether encoded by the gene or not, whether naturally-occurring or not, and whether in the D or L or meso form.

A discussion of the hydrophobic index as related to structure can be found in Eisenberg, D. R. M., et al., *Faraday Symp Chem Soc* (1982) 17:109–120, and in Janin, J., *Nature* (1979) 277:491–492. Of course, the index can be varied toward hydrophobicity by increasing the number of hydrophobic residues such as phenylalanine, valine, isoleucine, etc. Shifts toward a lower hydrophobic index can be effected by use of hydrophilic or charged amino acids. The hydrophobic moment is determined by the amphipathic quality of the peptide, which can be varied by adjusting the periodic hydrophobicity of the residues (Eisenberg, D., et al *Proc Natl Acad Sci USA* (1984) 81:140–144; Eisenberg, D., et al., *Nature* (1982) 299:371–374). The amphipathic property resides in the secondary or tertiary conformation of the peptide, resulting in portions or faces of the molecule which are water soluble and others which are hydrophobic. By taking account of conformation and the properties of the residues, this parameter can be readily adjusted. The lateral dipole moment is a reflection of the charge pattern due to the presence and placement of positive or negatively charged amino acid residues. The corrugation factor reflects the distribution of bulk and its effect on surface contours.

In more detail, the hydrophobic index (hi) is the sum over the amino acids in the peptide of the individual hydrophobic indices of the amino acid components. This can be formulated for a peptide of n amino acids by the formula:

$$hi(\text{peptide}) = \sum_{i=1}^{n} (hi)_i$$

The conformation-dependent parameters can be calculated by similar approaches which are, in each case, the modulus of the Fourier transform of the appropriate property function—i.e., the strength of the component of periodicity of period—delta, where "delta" is defined to match an alpha-helix (100°), or a beta sheet (170°). The assignment of the proper delta value will depend on the conformation normally assumed by the peptide, or that into which it is controlled by the designer of the peptide.

It is recognized, however, that the general relationships of the resulting parameters among members of a set do not appreciably change regardless of the assumptions made about the conformation. Thus, if the above parameters are calculated for all members of the set assuming, for example, an alpha-helix conformation, the resulting diversity in pattern will not vary appreciably even if the peptides in fact are not in the form of alpha-helices. This result is particularly important in regard to very short peptides of insufficient length to attain a recognized, ordered conformation.

Therefore, the calculations of the three parameters, hydrophobic moment (hm), dipole moment (dm), and corrugation factor (cf) are as follows:

$$\mu(\delta) = \left\{ \left[ \sum_{n=1}^{N} H_n \sin(\delta n) \right]^2 + \left[ \sum_{n=1}^{N} H_n \cos(\delta n) \right]^2 \right\}^{1/2} = \left[ \sum_{n=1}^{N} H_n e^{i\delta n} \right]$$

wherein for hm, H=hi; for dm, H=overall charge at pH 7; and for cf, H=volume.

The values of the characteristics of individual amino acids which are required to calculate the values of the characteristics of the encoded amino acids which are in turn needed to calculate these parameters as described above are given in Table 1.

TABLE 1

| | | hydrophobic index | pka | chg pH 7 | volume (A$^3$) | Rel freq |
|---|---|---|---|---|---|---|
| Ala | A | 0.25 | X | 0 | 91.5 | 6 |
| Asp | D | −0.72 | 3.86 | −1 | 124.5 | 6 |
| Glu | E | −0.62 | 4.25 | −1 | 155.1 | 6 |
| Phe | F | 0.61 | X | 0 | 203.4 | 4 |
| Gly | G | 0.16 | X | 0 | 66.4 | 7 |
| His | H | −0.40 | 6.0 | +0.1 | 167.3 | 3 |
| Ile | I | 0.73 | X | 0 | 168.8 | 4 |
| Lys | K | −1.10 | 10.53 | +1 | 171.3 | 7 |
| Leu | L | 0.53 | X | 0 | 167.9 | 7 |
| Met | M | 0.26 | X | 0 | 170.8 | 2 |
| Asn | N | −0.64 | X | 0 | 135.2 | 4 |
| Pro | P | −0.07 | X | 0 | 129.3 | 5 |
| Gln | Q | −0.69 | X | 0 | 161.1 | 4 |
| Arg | R | −1.76 | 12.48 | +1 | 210.9 | 4 |
| Ser | S | −0.26 | X | 0 | 99.1 | 8 |
| Thr | T | −0.18 | X | 0 | 122.1 | 6 |
| Val | V | 0.54 | X | 0 | 141.7 | 6 |
| Trp | W | 0.37 | X | 0 | 237.6 | 2 |
| Tyr | Y | 0.02 | 10.07 | 0 | 203.6 | 3 |

The sixth parameter, aromaticity, is provided by the inclusion of aromatic amino acids such as phenylalanine, tyrosine, and tryptophan among the naturally occurring amino acids, the D-forms of the naturally occurring residues, and other nonencoded amino acids such as P-aminobenzoic acid, and phenyl or naphthyl-β-alanine. The aromaticity of the resulting paralog, as encountered by an analyte, depends not only on the number of aromatic residues included, but also on the conformation of the molecule, as π-π interaction between the aromatic nuclei alter the electron cloud configuration. Aromaticity is a particularly important property when substances which are themselves aromatic in character are to be separated. As illustrated in Example 9 below, various members of the class of eleven phenol-based pollutants identified by the Environmental Protection Agency as particular problems can advantageously be separated and identified using paralogs which have aromatic properties and the appropriate paralog can be identified by variation of said aromatic properties among the panel.

The seventh variable, distance between charged atoms, is also conformation dependent. Computerized design models based on expected conformation and the nature of the charged groups can be employed to design paralogs which have predetermined spacings. This variable can be applied to peptides, but also is applicable to derivatized carbohydrates. Indeed, peptide-based paralogs can be designed which mimic the various multiples of charged moieties on the familiar chromatographic supports diethylaminoethyl cellulose (DEAE) (which provides spaced positive charges) and carboxymethyl cellulose (CM), which provides negatively charged atoms with predetermined spacing. Such variation in spacing is especially useful to provide a basis for size fractionation and to separate polymeric-charged molecules such as various DNA fragments.

The design of peptide paralogs further can take advantage of known properties of particular residues, such as the ability of α-aminoisobutyric acid (AIBA) to promote the formation of α-helices and the formation of disulfide bonds between cysteine residues to stabilize conformation. As the paralogs can be synthesized using nonbiological techniques, amino acids or their analogs with specifically designed side chains advantageous to confer the desired properties can be used.

An initial candidate panel can consist of about 90–100 peptides or related compounds for convenience. This is entirely a reflection of the design of commercially available microtiter plates and protein synthesizer rods (Cambridge Research Biochemicals) and is a convenient number to provide sufficient individual tests to frame the characteristics of the desired paralog. The synthesis is conducted using conventional, usually commercially available, methods.

A number of paradigms can be used to design the set having maximal diversity in the chosen parameters. In one protocol, the first formulated paralog, for example, will have each position filled by randomly chosen amino acids. The next candidate, also constructed by a random selection, will be compared to the first candidate for differences in the two or more measured and calculated parameters. Depending on whether there are substantial differences in these parameters, this candidate peptide will be retained or discarded. As more and more candidates are tested, of course, the greater is the likelihood that the candidate will have properties too close to one already in the set to warrant retention, and the larger number of candidates that will need to be formulated and screened before the member is retained in the set. The process will continue until the number of candidates examined since the last one was accepted becomes unacceptable. In general, the pattern expected is as shown below:

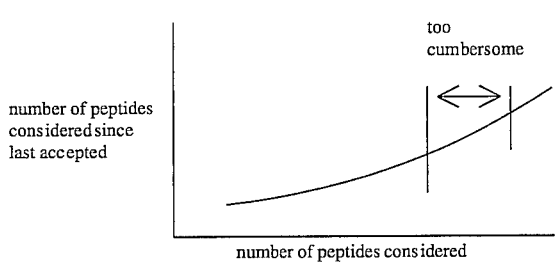

where the formulation and selection process should cease somewhere in the indicated region.

In order to obtain a final panel of 48, it is preferred to provide initially approximately 96 diverse candidates to permit final fine tuning by hand. For example, the dipole moments of the sidechains as compared to the dipole moment of the backbone might be considered. The final panel should be reviewed so that a distribution of properties exists for all varied parameters—i.e., each peptide differs from all others by at least X% (after normalization of the scale to the range of 0–100 units), the value of X being determined by the "cumbersome" zone on the graph. Thus, each peptide is substantially different from all other peptides in the set with regard to at least one of the two or more parameters. This approach is advantageous because computation is easier than synthesis. Full diversity is however, to some extent undermined due to thermally induced fluctuations in conformation.

The results of a computerized reduction to practice of this approach for preparation of a diverse set of 30 peptides averaging 6 amino acids is shown in FIG. 1. In this example, all five parameters were evaluated. The program creates random peptide sequences for which the five parameters are calculated wherein those with properties similar to the previously generated sequences are discarded. After trial runs to establish extreme values for each parameter, all five ranges were divided into three parts, thereby defining $3^5$ or 243 unique combinations of properties ("bins"). From the first about 200 random sequences of 6 mers proposed, 50 bins out of the 243 were filled. Filling the next 50 then required examining about 2,000 more sequences and additional thousands then contributed only about a dozen new combinations. With independent sets of randomly generated sequences, it was found that the same subset of bins was filled, implying that not all combinations are physically attainable with these monomers, for example a peptide cannot be both highly hydrophobic and highly charged.

As shown in FIG. 1, variations in isoelectric point and hydrophobicity are plotted along the X and Y axis respectively. The symbols within the field represent the conformation-dependent parameters measuring distribution of hydrophobic, bulky, and charged constituents according to X=high, squiggle=medium, and 0=low. This figure, thus, shows that a random set is conveniently designed.

As stated above, with respect to computerized design or otherwise systematic design, it is recognized that there are certain combinations of parameters that may not be possible—for example, the same paralog cannot easily be both highly charged and highly hydrophobic. It was found that only a modest number of peptides are needed to provide good coverage of all the known properties relevant to binding, described above. This is in agreement with previous work which has shown that considerable variability in the natural amino acid sequence is possible with little binding effect on interaction of antibodies with peptides. Lerner, R. A., *Nature* (1982) 299:592–596; Geysen, H. M., et al., *Proc Natl Acad Sci USA* (1984) 81:3998–4002.

Final selection of the peptide or other paralog panel is generally done manually to improve the evenness of sampling of the accessible portion of, for example, the 5-dimensional or a 7-dimensional peptide space.

A second approach to the preparation of diverse panels is analogous to that used for the preparation of ampholytes for isoelectric focusing. To prepare these ampholytes, dextrans are derivatized by conjugation to charged functional groups, typically sulfonates to provide negative charges and amino functionalities to provide positive charges. A random distribution of derivatization is produced in the reaction. The resulting ampholytes are then sorted by isoelectric focusing to provide ligands with a range of a single parameter—pI. For application to the invention herein, in this alternate approach, the compounds are randomly synthesized polymers which are then isolated by their ability to bind to a maximally diverse set of candidate paralogs which has been prepared by the designed systematic variation of at least two parameters. Thus, once an initial or model diverse paralog panel is designed, for example, as described above using peptides or their related compounds as the candidate panel moieties, the diversity of this panel can be used to segregate mixtures of other materials, including nonpeptide composite polymers, into a diverse set by specific binding of the members of the random mixture to each candidate peptide in the model paralog panel. This permits the synthesis of panels with superabundant diversity even for polymers which can be randomly varied by variation in the monomer units, but for which analytical appreciation of the specific two parameters associated with their chemical types is difficult.

Thus, although systematic direct calculation of aromaticity parameters and linear distance between charges in the case of peptides is more challenging than calculation of the distribution of the other five parameters, panels having diversity in these characteristics can be selected among randomly generated candidates with variations in these properties by using panels diverse by virtue of, for example, pI and lateral symmetry.

An extension of this method involves the reiterative interaction of two randomly-generated panels. The panels are alternatively checked against each other as diversity is added to both. Each candidate from, say, panel A is profiled with respect to panel B. Those candidates which have similar profiles to a previously-tested candidate are then discarded, or, stated in another way, at most, one of a group of candidates having similar profiles with regard to panel B is retained. This results in a panel A' with a diverse and greatly reduced number of members; panel B is then screened against the now diverse panel A' and, in a similar winnowing process, only one candidate member of a group having similar profiles is retained in panel B'. In general, panel B' will have a greater range of diversity than panel A'. The process is then reversed, screening the remaining panel A' members with regard to panel B' and the process is continued until the desired degree of diversity is obtained. In short, an initial panel of candidates is obtained either by calculation or simply by random selection from a large diverse set. The large diverse set is then categorized with respect to differential binding to the initial set; well separated members of the .set are then used as the next approximation to a maximally diverse set.

It has been noted above that the paralogs need not be constructed of peptides or their close relatives. Additional embodiments which permit variability of at least two measures of properties analogous to those set forth above for peptides can also be used. The only requirement is that the paralogs be constructed of variable parts so that their properties can be systematically varied. For example, nucleic acid sequences are known to have different specific binding properties with respect to various proteins. Indeed, it is understood that the regulation of gene expression occurs by virtue of these specifically-binding proteins which have a specific affinity for particular sequences in the genetic material (see, for example, Tjian, R., et al., *Science* (1989) 245:371–378). While many of the parameters associated with peptide variability, such as pI and hydrophobicity index are difficult to vary in this case, other parameters such as GC/AT ratio are conveniently made to fall into values over a range. In addition to overall GC/AT ratio, the placement and variation of GC and AT on a single strand, the number and placement of homopolymeric stretches (such as AAAA and GGGG), and the nature and placement of symmetric regions in the strands can also be varied. In the case of symmetric regions, it is known that those which represent dyad-type symmetry—for example GATXATC (commonly misidentified as palindromic sequences) are known to permit formation of intrachain loops due to base pairing, and are also prominent among sites recognized by dimeric proteins, including several restriction enzymes. True palindromes such as GATTAG have different effects on properties. In any case, the foregoing provides a number of parameters, any two of which can be maximally varied to produce the paralog panels of the invention. As nucleic acids are readily synthesized, use of these polymeric compounds as candidate paralogs has considerable advantage. Also, because it is known that specific nucleic acid/protein interactions occur, randomly constructed nucleic acid mixtures could be segregated by binding to individual members of the diverse peptide panel described above.

Further, the availability of the polymerase chain reaction (PCR) has permitted the synthesis of DNA (or RNA) sequences which bind specifically to any target molecule, including proteins. Thus, an inverse panel corresponding to the maximally diverse peptide panel of candidate paralogs can be constructed by taking advantage of these methods (Tuerk, C., et al., *Science* (1990) 249:505–510; Ellington, H. D., et al., *Nature* (1990) 346:818–822). This process too can be iterated. Binding of candidate nucleic acids to a panel of diverse peptide yields a second nucleic acid panel which is more diverse.

Methods for constructing nucleic acid polymers of predetermined and arbitrary sequences are well established. While appropriate DNA fragments could, in principle, be isolated from natural sources and utilized in accordance with the methods of the invention, it is clearly preferable to design and synthesize nucleic acid sequences with the required diversity of properties de novo. Commercially available methods include solid phase-based synthesis of DNA fragments of more than sufficient length to represent the paralogs of the invention.

A similar approach is convenient in preparing alternate paralog forms such as those formed by copolymers of hydrophilic and hydrophobic components such as combinations of polyethylene and polyethylene glycol subunits. Alternate hydrophilic/hydrophobic or even potentially charged monomeric units such as methacrylic acid can be used in these constructs. For example, copolymers of PEG and polyvinyl chloride or of methacrylic acid and propylene, and the like can be formed, and then segregated into maximally diverse embodiments.

Similarly, carbohydrates can be derivatized with charged groups such as sulfates and amines at various random levels and segregated according to their diverse properties, not just pI, thus giving sets with finer capacity for discrimination for use in, e.g. displacement chromatography. Phosphodiglycerides can also be constructed which have a variety of properties.

It is, of course, recognized, that while diversity among the panel members can most conveniently be calculated when all panel members are of the same general character—i.e., peptides, carbohydrates, nucleic acids, etc.—there is no theoretical reason why a panel could not be constructed using mixtures of these representative paralog types, since the goal is a panel maximally diverse in electron cloud pattern, not symbol manipulation. Thus, a paralog candidate panel could reasonably be comprised of peptides, carbohydrates, copolymers, etc., as long as the diversity of the parameters selected is maintained.

It is thus a function of the invention to provide panels of maximum diversity which can then be subjected to screening procedures to obtain the most desired paralog for the application at hand. The panels can be packaged into kits for conduct of the screening procedures. A further description of such kits follows the description of the screening method which is set forth below.

Screening Procedures

In one approach, the procedure to screen the panels for the most advantageous candidate paralog can be used repeatedly because the binding-based assays used to detect specific affinity are generally reversible so that the testing compositions can subsequently be removed from the paralog panel which remains bound to solid supports. It is not necessary to perform such assays in a recoverable form or bound to solid supports, but it is highly convenient to do so.

The reusability is particularly convenient in the context of one of the intended uses of the paralog—as an affinity ligand in chromatography, since the relative binding strengths in a series of proposed elution solvent systems can be tested systematically. For example, the strength of binding in a series of solutions containing methanol at increasing concentrations or solutions at increasing salt concentrations simulating elution gradients can be used. In this type of testing the comparative behavior of a number of paralogs under a multitude of elution conditions can be tested empirically. This may be very helpful in that the binding constant gradient obtained for paralog X may be preferable to that obtained for paralog Y under desired elution conditions even though paralog Y might appear to have a preferable specific affinity level when tested under only one solvent or temperature condition. The reusability of the test panel thus permits the selection of the best paralog under a pattern of conditions which simulates its use in the chromatographic procedure.

Figure 2:
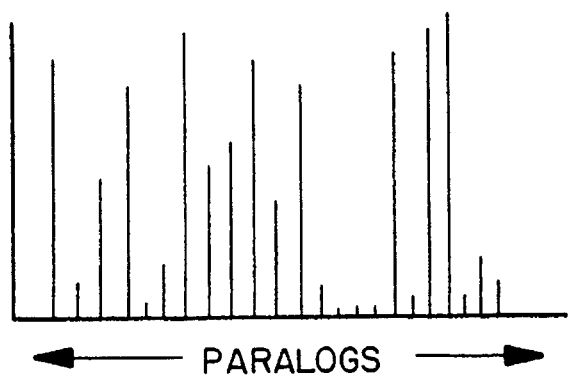
FIG. 2 shows the generic results of a typical ELISA binding assay wherein a panel of paralogs is reacted with a single labeled analyte.

However the panel is formulated for testing, the panel is then tested for specific affinity of its members to the selected moiety. On a theoretical basis, one might do this directly by labeling the moiety and detecting the relative amount of label bound to the individual paralog members of the panel. Using this approach, a pattern similar to that shown in FIG. 2 will be obtained. As shown in FIG. 2, the amount of label bound to each member of the panel (the y coordinate) is shown across the members of the panel (the x coordinate). Varying amounts of labeling are obtained, depending on the affinity of each paralog for the moiety. "Labels" such as enzymatic activity or other detectable property of the moiety can also be used.

An alternative to this direct method is sometimes more practical. In this alternative, specific affinity is assayed by means of competition of the unlabeled moiety with a mixture of labeled peptides or other suitable ligands. The mixture must contain a sufficient number of members so that more or less equivalent binding to all paralogs by the labeled mixture per se in the absence of moiety is obtained. This general approach for detecting binding of an unlabeled substance to members of a panel is described in more detail in PCT publication WO89/03430, published 20 Apr. 1989.

Briefly, the mixture of the requisite number of random ligands (roughly on the order of 500–1000, although in some instances smaller numbers may suffice) is labeled in a suitable manner, for example, in the case of peptides, using the acyl iodination method with the iodine isotope 125 as described by Bolton, A. E., et al., *Biochem J* (1973) 529–539, and available commercially from ICN Radiochemicals. The mixture can be prepared directly by synthesis of individual members and mixing them together or, more conveniently, can be obtained by hydrolysis of large proteins or other polymers into random small peptides or other oligomers. One approach, for example, utilizes a partial trypsin hydrolysate (Cleveland, D. W., et al., *J Biol Chem* (1977) 252:1102–1106) of a yeast lysate. This provides a large number of peptides which can be labeled as a mixture, or which can be separated using, for example, SDS gel electrophoresis and transferred to a test support such as Immunodyne (Burnette, W. N., *Anal Biochem* (1981) 112:195–203, if their binding is to be assessed individually.

Figure 3:
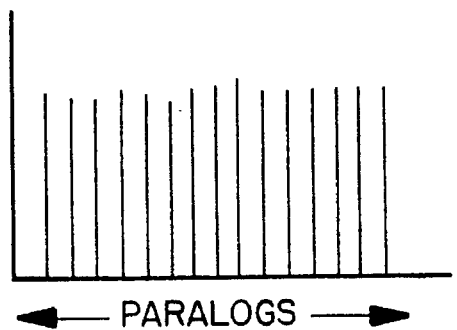
FIG. 3 shows the generic results of a typical ELISA binding assay wherein a panel of paralogs is reacted with a mixture of labeled peptides.

It may be necessary in utilizing the labeled ligand mixture to verify that satisfactory binding occurs with regard to all candidate paralogs in the panel. The conditions for effecting this equivalent binding throughout the panel should also be established empirically. In a perfect situation, the ligand mixture will bind uniformly to all panel members as shown in FIG. 3A. However, more frequently, only similar levels of binding are found, as in FIG. 3B. This provides a perfectly workable basis for competition with analyte. Interpretation of results when competition is added can be simplified by normalization of the binding values to the same value before evaluating the competition.

Figure 4:
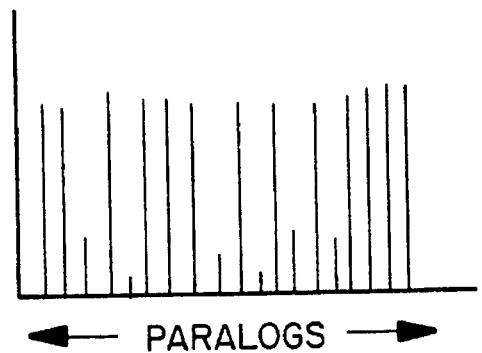
FIG. 4 shows the generic results of the corresponding assay of the same paralog panel with the labeled mixture in the presence of unlabeled analyte.

When it is confirmed that the labeled ligand mixture binds roughly equivalently to all candidate paralogs in the absence of selected moiety, or similar binding has been normalized, the screen is repeated in the presence of the desired moiety, such as an analyte. Those candidates which have specific affinity for this moiety will show a decrease in the conjugation to labeled ligand mixture, the decrease being proportional to the specific affinity of the candidate for the moiety. A typical competition pattern is shown in FIG. 4. The meaning of the coordinates is the same as in the other figures. The paralogs with greatest affinity to the selected moiety, however, show the lowest levels of labeling as this indicates successful competition of the selected moiety with the labeled ligand mixture for the paralog. By assessing the ability of the moiety to compete, those paralogs which show the greatest decrease in label uptake are selected as having the parameters that are most favorable for binding selected moiety.

The screening process can be repeated with additional panels having properties intermediate to those members which show the greatest specific affinity or the most desirable elution pattern behavior in the original panel, in order to fine-tune the molecular shape and charge distribution pattern of the ultimately chosen paralog. The screen can be repeated an arbitrary number of times with an arbitrary number of panels to the degree of specific affinity or the chromatographic behavior required. The electron cloud pattern of the paralog panel can thus be systematically manipulated to optimize the affinity of the paralog for the selected moiety; if the paralog will be used as an affinity ligand in a chromatographic procedure, an affinity that is so great that elution is difficult may not be desirable, and the correct pattern should be chosen. The effect of conformation control can also be studied, as described above.

Figure 5:
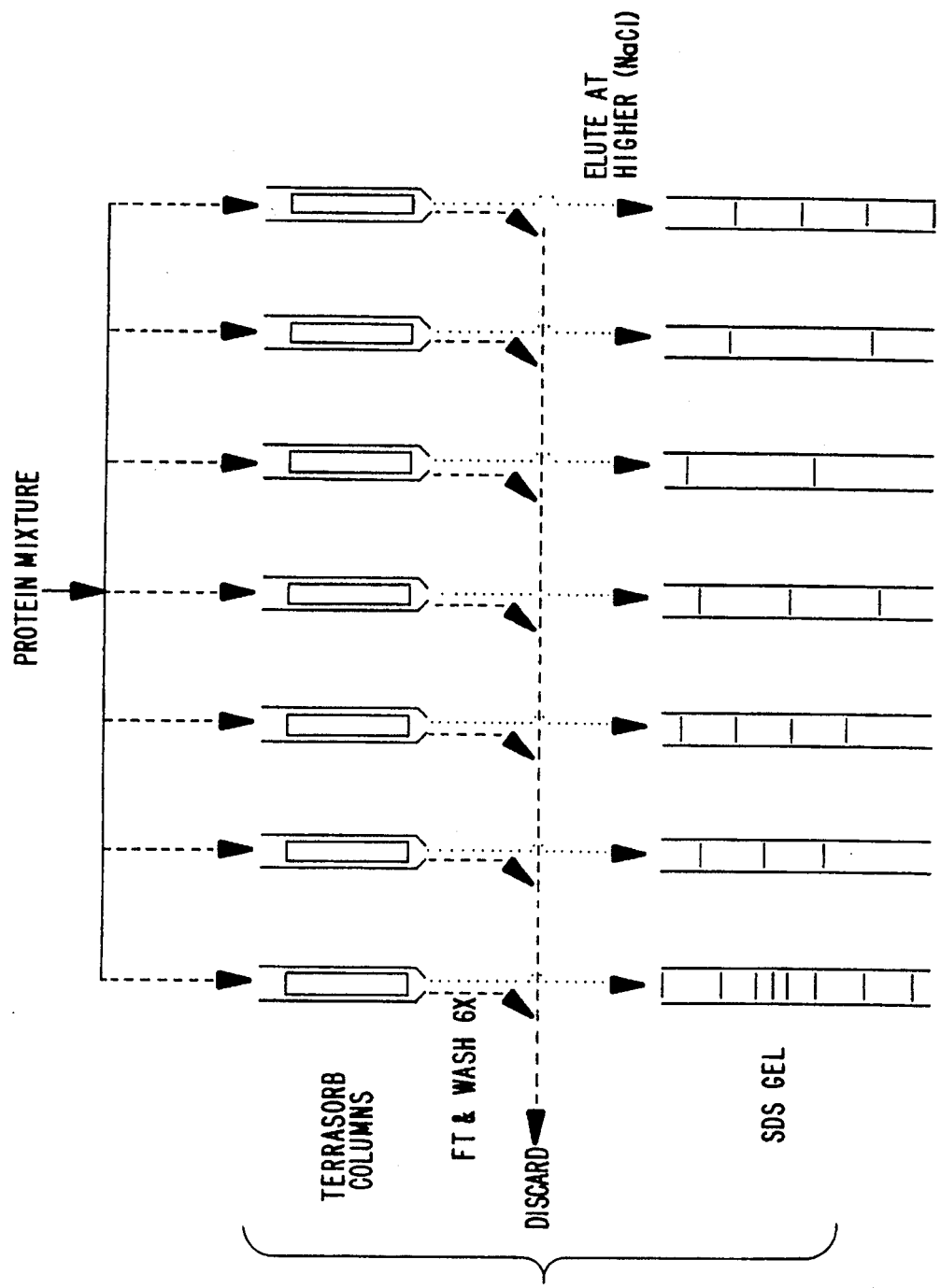
FIG. 5 shows a schematic of a chromatographic kit to determine proper paralog ligands for separation of a desired mixture.
Figure 6A:
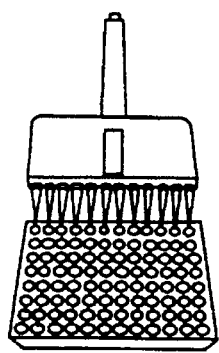
FIGS. 6A, 6B, 6C, 6D, and 6E show a schematic of the determination using the kit of FIG. 5 conducted on a microtiter plate.
Figure 6B:
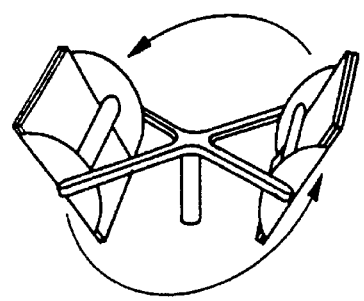
Figure 6C:
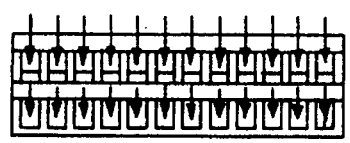
Figure 6D:
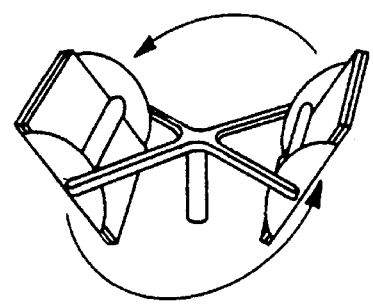
Figure 6E:
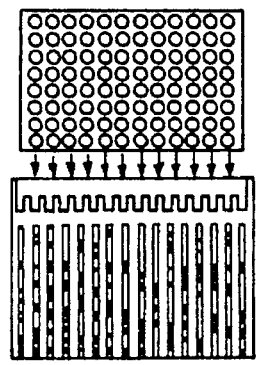

In an alternative embodiment, the paralogs can be packaged in a manner intended to simulate their intended use by conjugation to solid supports which are then packaged as chromatographic minicolumns as shown schematically in FIG. 5. A desired number of columns representing diverse candidate paralogs are then contacted with the protein or other mixture containing the desired analyte. The flowthrough volume is discarded and the columns are then eluted with a suitable elution solvent, such as concentrated salt. The eluates are then examined for the presence or absence of the desired analyte.

In the representation shown in FIG. 5, the eluates are subjected to analysis by SDS-PAGE to determine the pattern of analyte adsorption from a protein mixture. As shown in the figure, the diverse paralog set is able to adsorb and elute different proteins from a complex mixture employed as a test sample.

FIG. 6 shows a still schematic, but somewhat more detailed, diagram of the approach outlined in its simplest form in FIG. 5. As shown in FIG. 6, the sample is loaded using, if desired, a multiplicity of pipette delivery tips into the wells of a microtiter plate which is provided with a set of miniature chromatographic columns as shown in FIG. 6C. These minicolumns are juxtaposed with an additional microtiter plate to collect flowthrough, also as shown in FIG. 6C. After loading the samples as shown in FIG. 6A, the unbound fraction is collected by centrifuging the plate layers to drive the liquid through the minicolumns into the receiving plate (FIG. 6B). The unbound fractions are saved, if desired, or otherwise are discarded. The minicolumns are then eluted using any convenient buffer or other eluant, and the eluant fractions are the collected by centrifugation. Either or both of the flowthrough volumes containing unbound fraction and the eluant containing adsorbed fraction can be analyzed using parallel samples on SDS gels as shown. Any method for developing the gels can be used; silver staining, because of its general applicability, is preferred.

Membrane-bottomed microtiter plates are available commercially, e.g., from Pall Corporation. These microtiter plates contain membranes at the bottom of the wells which are capable of supporting a settled bed of solid support. The membranes do not pass fluid unless a pressure differential is applied by vacuum or by centrifugation. Thus, the sorbents in the wells can be tested as pseudochromatographic columns by applying the appropriate solutions and then passaging the solutions through the column by creating the required pressure gradient.

Figure 7:
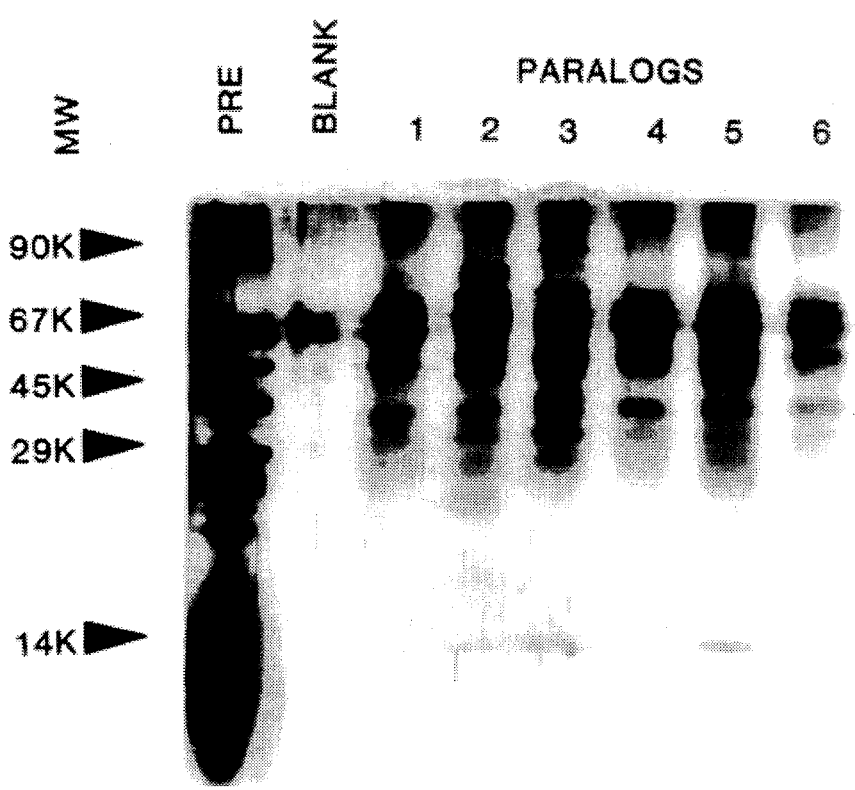
FIG. 7 shows the results of application of a yeast lysate to a series of six paralog columns.

The results of this approach as applied to a yeast hydrolysate and a series of six paralog columns is shown in FIG. 7. In this illustrative experiment, a total cell lysate of yeast (Sigma Y-2875) was partially purified on DEAE cellulose and the portion binding to DEAE cellulose between 50 and 150 mM NaCl was isolated and dialyzed against 10 mM Tris HCl buffer, pH 7.5, at 10 mg/ml. A sample of 100 ul was applied to a series of 0.15 ml bed volumes in minicolumns filled with Affigel (BioRad) derivatized with 2 umoles paralog per ml settled bed volume. After unbound proteins were washed through, the columns were eluted with 250 mM NaCl and the pattern of bound proteins analyzed by SDS gel-electrophoresis.

Lane 1 of FIG. 7 shows the pattern obtained from the material loaded onto the columns; lane 2 shows the results of elution of the mixture when underivatized support was used as the column; virtually no proteins were eluted, and the electrophoresis gel shows the common doublet silver stain artifact at 65 kd. This artifact is believed to be due to a combination of the ubiquitous keratin protein and oxidized dithiothreitol. The results of the remaining six lanes 3–8 indicate that different proteins are adsorbed and eluted from different paralogs.

Other configurations for test panels can, of course, also be used.

In addition to the use of the screening method of the invention to identify specific paralogs which can be applied in various therapeutic, analytical, diagnostic, and other applications, the screening methods can also be used to create matrices indicative of interaction between molecules. Thus, a pattern of reactivity across the entire panel with respect to an alternate panel of any desired diversity generates a large number of data points indicating the strength of the interaction. For example, a 15-member paralog candidate panel cross-reacted with aa 15-member test panel generates 225 ($15^2$) data points which can be correlated with structural features accounting for the variation in strength of interactions. Correlation coefficients can be calculated and used to select a subset for retaining the highest degree of diversity available. Such cross binding tables are also useful in preparing panels for competition binding such as that shown in FIG. 4, where uniform binding of all the members of one panel with regard to the cross reacting panel is desired.

Use of the Selected Paralogs

When a paralog of suitable specific affinity for a selected moiety is found according to the method of the invention, the application of the selected paralog is appropriate wherever such specific affinity is required. In addition to utility as a specifically binding ligand on a chromatographic support for separation of an analyte from contaminants, the ability of the paralog specifically to bind the selected moiety may be employed by using the paralog as a specific binding reagent in an assay, analogous to an immunoassay, which depends on this specific interaction. In addition, if the selected moiety is a receptor or other biological target, the paralog will be useful in a variety of pharmacological and therapeutic applications, e.g. to provide information and data for QSAR and computer modeling.

For use in chromatography, when a paralog with satisfactory characteristics for a desired analyte is chosen, it is conjugated to a solid support using conventional means known in the art. Typical solid supports include polysaccharide supports, acrylamide gels, silica supports, alumina, and the like across the range of typical commercially available chromatography supports. It should be noted that in addition to particulate chromatographic supports, membrane type supports are also commonly used. A number of chromatographic membranes are available commercially. A wide variety of conjugation techniques is also available including those which introduce a linking arm, if desired, between the solid support and the paralog ligand. The use of a linking arm of a length equivalent to at least 3–9 carbons is advantageous in some instances in order to provide greater accessibility of the analyte to the ligand.

In addition, the spacing of the paralogs on the support can be controlled to provide the desired degree of affinity for the analyte or other substance to be retrieved. The ability to space the ligands at will is advantageous in that it permits control of the number of theoretical plates in a particular column. The higher the density of the affinity ligand, the higher the number of theoretical plates that can be obtained. As the paralogs of the invention are relatively small molecules as compared to most affinity ligands, the potential number of theoretical plates on the same size column is correspondingly higher. The paralogs can be designed to couple to specific molecular motifs on the solid support with which they can react. Methods for conjugating materials to solid support include coupling to hydrazide-derivatized supports, such as those described by Wilchek, M., et al., *Meth Enzymol* (1974) 34:475–479, or use of photoclearable moieties that generate reactive species to react with the support as described by Eberle, A. N., et al., *Meth Enzymol* (1985) 109:129–156.

The resulting substrate, comprising solid support (particulate or membrane) conjugated to a paralog specific for binding to the desired analyte, can then be used in a manner conventional for chromatographic substrates. Particulate supports can be packed into columns or placed in filter beds to adsorb the analyte when the composition containing the analyte is contacted with the substrate. Since the paralog is a relatively stable ligand, preparations and columns packed with the invention substrate can be included in apparatus designed for HPLC.

The advantages of adapting affinity-based chromatography to HPLC cannot be easily overestimated, especially if the chromatographic procedure is conducted on a preparative scale. Resolution in preparative procedures needs to be achieved on the basis of the characteristics of the column rather than the brute force methods of increasing the size of the column or adjusting the strength of the eluant downward so that elution will take a longer time period. Any adjustment which increases the complexity or amount of eluting solvent is a serious drawback on a preparative scale. For example, expensive solvents and complex mixing protocols are reasonable when a total of 10–100 ml is required as in analytical procedures; they become expensive and problematical when hundreds of gallons are required as is often the case in preparative protocols. Not only does the solvent need to be recovered in order to lower the cost, an expensive process in itself, but it also needs to be removed from the product being prepared.

In addition, since material purified by preparative chromatography is generally required to be recycled through the column to effect adequate resolution, complex elution protocols have the additional disadvantage of requiring reequilibration of the column in the recycled phase. Faster reequilibration is also advantageous for analytical separations done in large numbers as is the case for most industrial applications.

For the foregoing reasons, in general, analytical procedures become scalable only when the basis for the separation is selectivity of the absorbent—i.e., is based on an affinity chromatography approach.

In one particularly preferred protocol, a column can be constructed having a series of paralogs of varying, generally increasing, affinity for the target analyte. The succession of binding affinities as the analyte travels through the column is effective in improving resolution. In a typical embodiment, the column begins with a paralog ligand which has very low affinity for the target; the paralogs to follow have increasing affinity. Contaminants are thus retarded with respect to the desired analyte which progresses through the column more readily.

Accordingly, columns packed with substrate having paralog ligands can be used as either analytical or preparative tools, and the use of paralog-derivatized substrate columns provides a convenient and efficient alternative to more conventional chromatographic approaches. If the analyte is a drug, the paralog-derivatized substrate can be used as a specific reagent to adsorb the drug from body fluids and the drug can then be recovered for analysis. If the analyte is a toxin appearing in waste products, the substrate can be used for detection, and also for removal of the toxin from the mixture. If the analyte is a desired product made in low yield, the sorbent can be used to isolate the product batchwise or using standard chromatographic techniques.

An additional use of diverse sorbents is to improve analytical identification. Traditional practice in TLC identification of analytes, for example, utilizes two or more solvent systems often run on the same plate at 90° angles. Analyte must match the reference $R_f$ in both systems for positive identification. Panels of diverse sorbents likewise generate profiles which can be used for analyte identification.

It might also be noted that, as for the most part paralogs are chiral molecules, paralog-based columns may be employed for the direct separation of an enantiomeric mixture and other chiral preparations.

Advantage can also be taken of those paralogs which have the property of specific affinity for toxins by using them as scavengers in vitro and in vivo. For example, in one embodiment, latex beads conjugated to paralog might be delivered to the intestines or the bloodstream as an antidote to poisoning or used in more conventional extracorporeal applications. In another embodiment, such configurations might be used as delivery systems for drugs which bind specifically, but with moderate affinity to the paralog, particularly in cases where the paralog-drug combination provides properties which permit taking advantage of the ability of the paralog to bind receptors associated with physiological transport, such as cases wherein the drug must cross the blood-brain barrier or enter solid tumor tissues.

As stated above while the selected paralog has utility when conjugated to solid support, especially in chromatography, the utility of the paralog is not limited to its solid-bound form. The paralog of appropriate composition and characteristics can also be used to substitute for the corresponding antibody or fragment thereof in standard immunoassays. For use in this manner, the paralog may or may not be labeled, depending on the protocol. For example, in a typical sandwich assay, microtiter wells coated with paralog are used to test samples for antigen, wherein antigen bound to paralog is then labeled using the labeled form antibody specific for a different epitope or with the labeled form of an alternate paralog. Or, labeled paralog can be used to compete with any analyte antibody in a sample for antigen bound to solid substrate. As is well understood in the art, the variety of specific protocols for solid phase-based and agglutination-based immunoassays is vast and well understood by practitioners of the art.

In addition to the coupling of a single or simple mixture of the paralogs to a solid support, gradient-type supports can be prepared by distributing the members of the mixture along the support. Thus, a series of affinities can be constructed along the surface or length of a support to accommodate variations in substance best adsorbed. For example, the foregoing approach is particularly attractive for use in DNA sequencing gels. Standard gel systems provide for separations of several centimeters gel length for fragments of 50–51 bp, but only tenths of millimeters for fragments of ten times this size, which limits the amount of sequence information that can be obtained from one gel. Gels carrying a paralog affinity gradient resulting from distribution of paralogs of varying affinities to DNA could compensate for the size separation parameters either alone, or in combination with other prior art modifications to the technique which have attempted to compensate for this problem. Adjustments of affinity for various DNA segments among paralogs can readily be made by varying the linear distance between positively charged atoms. The gels can be constructed in the conventional manner, or can be constructed as thin surfaces on nitrocellulose or cellulose acetate membranes.

Figure 16A:
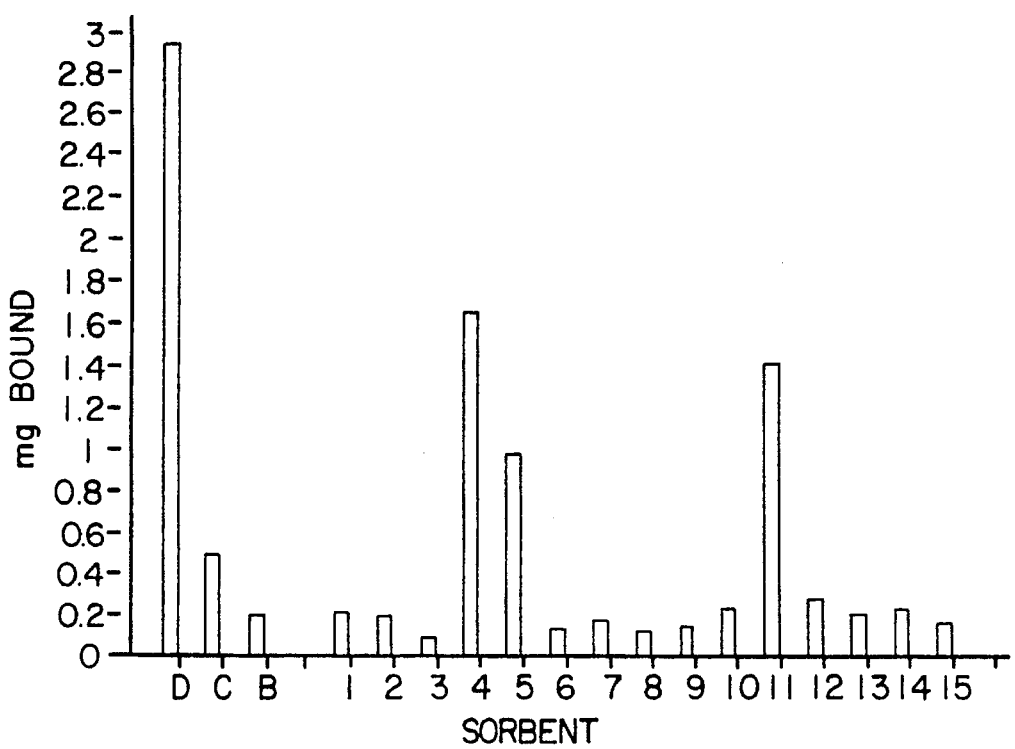
FIG. 16 shows binding profiles of single proteins with respect to a paralog panel.
Figure 16B:
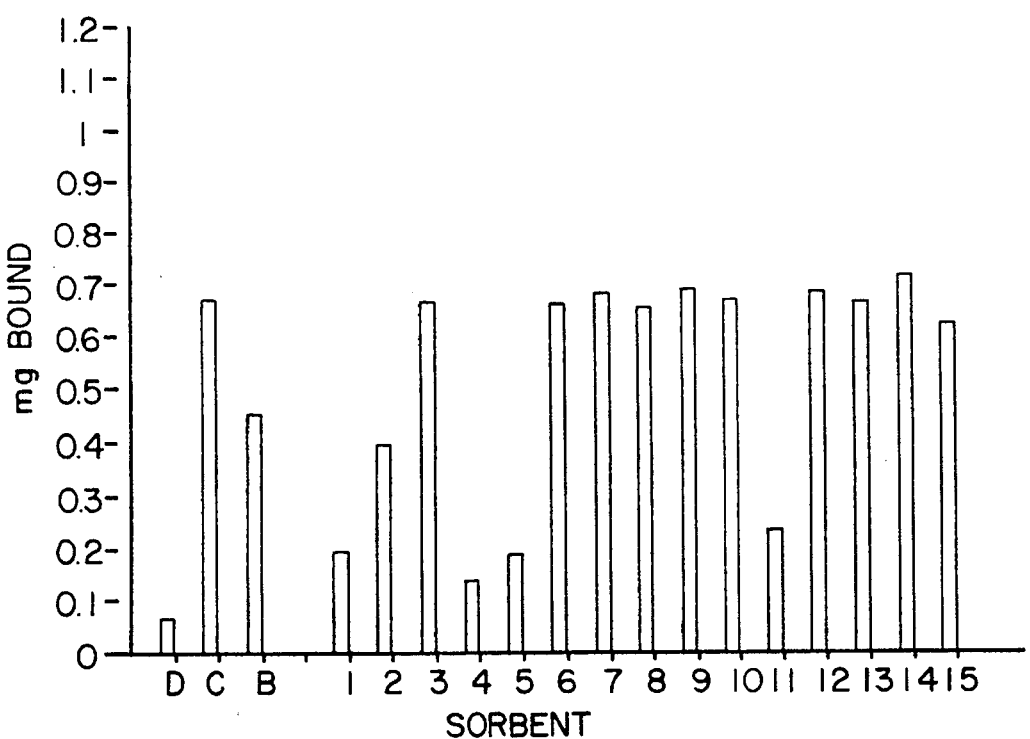

An additional utility for the paralog panels per se is in characterization of analytes by obtaining suitable profiles such as those shown in FIGS. 2, 4 and 16. The level of characterization obtainable in this way exceeds that generally obtained in the prior art by using chromatographic analysis, even in two dimensions.

The following examples are intended to illustrate but not to limit the invention.

EXAMPLE 1

Design of a Paralog Panel

Figure 9:
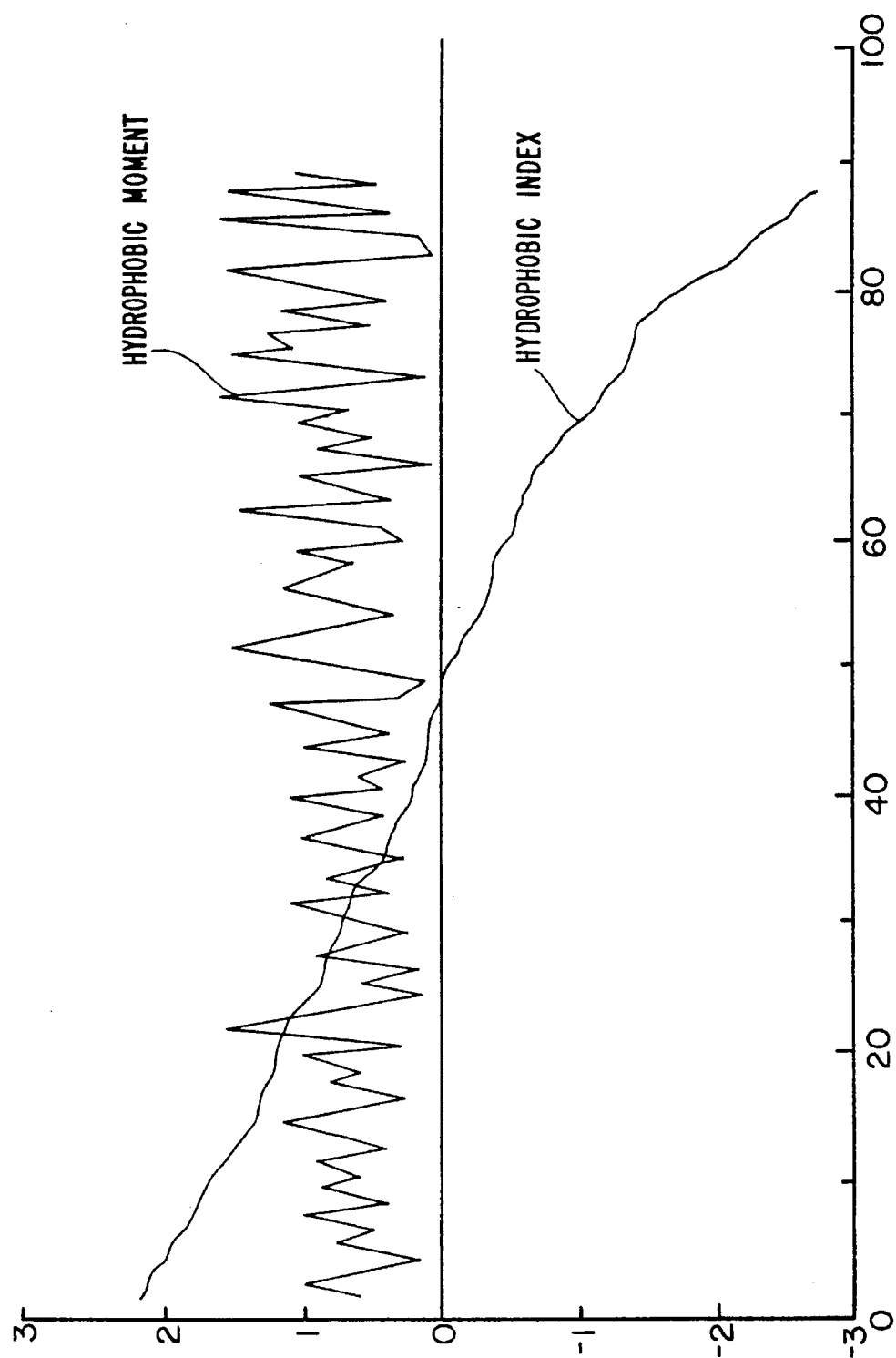
FIG. 9 shows the variation in hydrophobicity index and hydrophobic moment across the panel of FIG. 4.

A panel of 88 pentapeptides is designed on the basis of decreasing hydrophobicity and periodic variation of hydrophobic moment. FIG. 8 shows the list of pentapeptides synthesized numbered 1–88, along with 8 additional controls for use in synthesis according to the method of Geysen, H. M., et al., *Proc Natl Acad Sci USA* (1984) (supra); FIG. 9 shows the hydrophobic index and the hydrophobic moments across this panel.

The panel is synthesized using the commercial version of Geysen's technique (Cambridge Research Biochemicals) or any other convenient multiple peptide synthesis format. The panel is then probed with a protein for which a label is available, and the pattern of binding established. When a reasonable number of successful candidate paralogs has been obtained, these successful candidate paralogs are synthesized using routine peptide synthesis methods in sufficient quantity to verify their sequence and perform additional chromatographic experiments. The peptide is linked to the solid support Affigel 10 (BioRad) and packed into a column, or the chromatographic support is obtained by allowing the peptide to remain on the silica-based support Ultra-Affinity® (Beckman) upon which it was synthesized.

In order to verify that the paralog has the required specific affinity, a similar column can be prepared using a scrambled form of the paralog's amino acid sequence as ligand. The analyte in many cases will bind to the paralog-containing column, but not to the scrambled peptide-containing one. The Atassi references (supra) confirm that such scrambling may destroy binding.

EXAMPLE 2

Cyclization of Paralogs

A. Three paralogs of dissimilar properties, KNRGFK, KGYLYLYK and GKUIUIUK (where U=para amino benzoic acid and other letters refer to standard amino acid code), each containing available lysine residues, are attached, at pH 6.5, through their N-terminal amino groups to Baker-bond CBX beads previously derivatized with N-hydroxysuccinimide. After coupling, the lysine residues are intramolecularly joined using the homobifunctional cross-linking reagent difluoro-dinitrobenzene. A color change is used to monitor the reaction (single point reaction with the cross-linker yields a faint yellow color; full cross-linking yields a dark yellow color). The beads are packed into a standard stainless steel chromatography column using a slurry packer.

B. Cyclization alters the properties of a paralog by three major mechanisms. First, it reduces the conformational freedom of the backbone; second, it creates a partial cavity into which analytes may insert; and third, it alters the level of aromatic character perceived by the analyte. The cross linker itself also introduces useful aromatic character. FIG. 10 shows chromatograms of the hydrophobic analyte insecticide DDD on columns prepared as in paragraph A after cyclization, along with controls using underivatized CBX sorbent and NHS-derivatized CBX blocked with ethanolamine. As shown in the figure, the DDD peak is progressively later eluted from the supports: blocked CBX, cyclized GKUIUIUK, cyclized KGYLYLYK and cyclized KNRGFK.

EXAMPLE 3

Design of a Diverse DNA Panel

FIG. 11 shows an illustration of a computer program designed to generate nucleic acids of diverse values of four properties: total G/C percent; number of G/C regions; level of direct symmetry; and level of complementary strand (dyad) symmetry. For each property, the low value was assigned the value of 1 and a high value was assigned a value of 2. By use of the program, the results of which are shown in FIG. 10, a 16-member panel with maximum diversity in these four properties was designed. As shown in the figure, for each 20-mer synthesized, the first line gives the sequence generated and the successive four lines gave parameters used in calculating the property descriptors. The bin number is characterized by the pattern of 1 and 2 designations of the four properties; the actual values of the properties associated with these designations are shown in the next line.

The 20-mers thus designed are then synthesized using standard solid-phase techniques for coupling to suitable supports and construction of the paralog panel.

EXAMPLE 4

Construction of Paralogs of Polymers mimicking Predetermined Properties

A series of paralogs designated B85-4; B85-22; B85-31; B85-40; and B85-37, which have amino acid sequences as follows:

B85-4: Aib-Asp-Asp-Asp-Asp-Asp

B85-22: Aib-D-Phe-Asp-Asp-Ser-Ser-Orn

B85-31: Aib-Cys-Asp-Asp-Asp-Asp-Cys

B85-40: Aib-Cys-Asp-Orn-Orn-Orn-Cys

B85-37: Aib-Cys-Orn-Asp-Asp-Orn-Cys.

These peptides were synthesized according to the procedure set forth in Example 1. The paralogs were coupled to Affigel 10 at pH 7.5 and applied to the Pall Corporation Silent Monitor® 96-well flowthrough microplate by filling the wells with 175 microliter settled bed volume of coupled support.

A crude yeast cell lysate (Sigma) was freed of nucleic acid fragments by treating the lysate with DEAE cellulose in TE buffer (Tris-HCl, pH 7.5, 1 mM EDTA), followed by binding to CM cellulose and elution with TE buffer plus 500 mM NaCl. The resulting soluble protein, designated YX/DC-500 was concentrated threefold by lyophilization and dialyzed against TE buffer.

Aliquots (50 µl) of the protein solution were applied to each well using a multichannel pipetter. This was followed by three loading buffer washes of 150 µl and then with two elution buffer washes of 100 µl each. The eluting buffer is TE plus 250 mM NaCl. The eluates are collected in recipient microtiter plates and applied to SDS gel electrophoresis which is visualized by silver staining.

Figure 12:
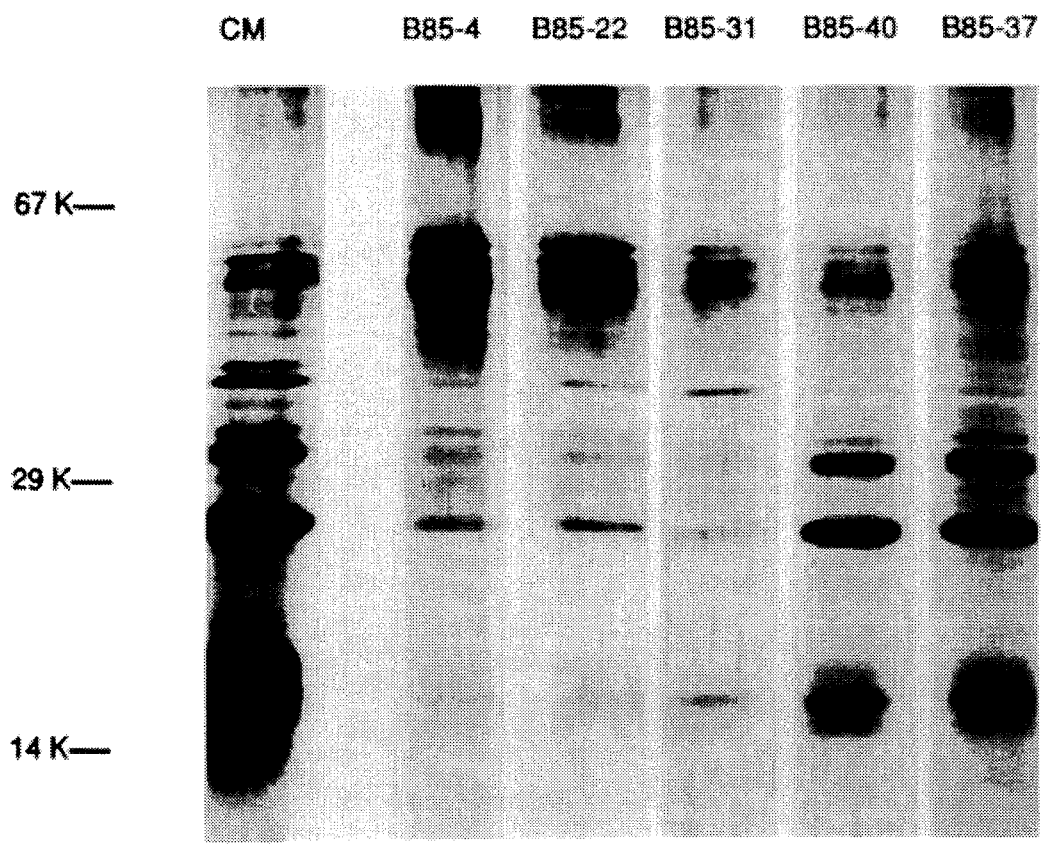
FIG. 12 shows the ability of paralog embodiments to mimic carboxymethyl cellulose to a predetermined degree.

FIG. 12 compares the results obtained when carboxymethyl cellulose (CM) or the various paralogs of the invention were used in the minicolumns. As seen, the behavior of CM with respect to any particular protein band can be mimicked in the paralog. For example, B85-40 and B85-37 give results similar to those for CM with the protein bands at 28 and about 35 kd; on the other hand, B85-31 and B85-22 show different behaviors with respect to these proteins but a more analogous behavior with respect to the band eluting at a position corresponding to about 55 kd. Thus, the behavior of CM with respect to any desired component band can be maximized or minimized.

EXAMPLE 5

Use of Paralog Supports as Post-Separation Techniques

The effect of rerunning a peak activity fraction from an initial chromatographic separation on the same sorbent (in this case DEAE) or on a different sorbent (in this case the paralog of B85-29, having the structure Aib-Cys-Orn-Orn-Orn-Orn-Cys) is compared in this example. The crude yeast lysate was applied to DEAE and eluted using a steep-step salt gradient for elution. The fraction eluting between 90 mM and 110 mM was then run on either DEAE or the B85-29 sorbent column in 1 ml open gravity flow columns using a shallow step salt gradient for elution. Most of the proteins which eluted between 90 mM and 110 mM NaCl on the first DEAE column continued to do so on the second DEAE column. However, about a third of the material does not bind to the parallel B85-29 column, and the bound proteins elute over a broader NaCl concentration range. These results are shown schematically in FIG. 13 and the actual results as visualized on SDS-PAGE gels are shown in FIG. 14.

Figure 13A:
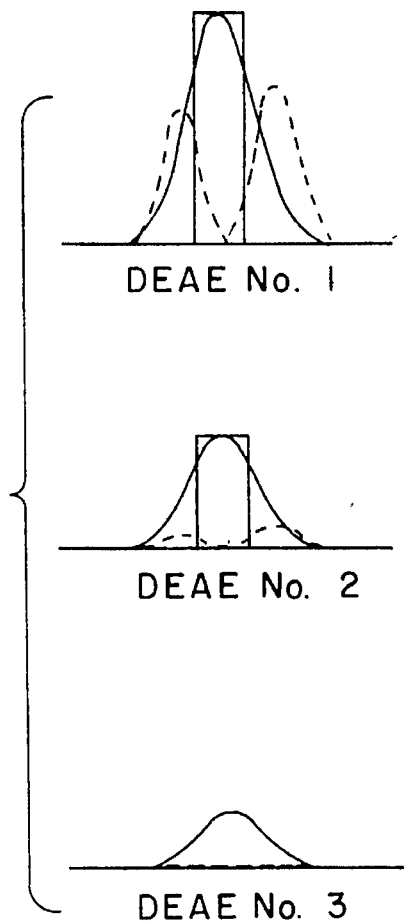
FIG. 13 is a diagrammatic representation of the use of a paralog column analogous to DEAE as a post-separation technique.
Figure 13B:
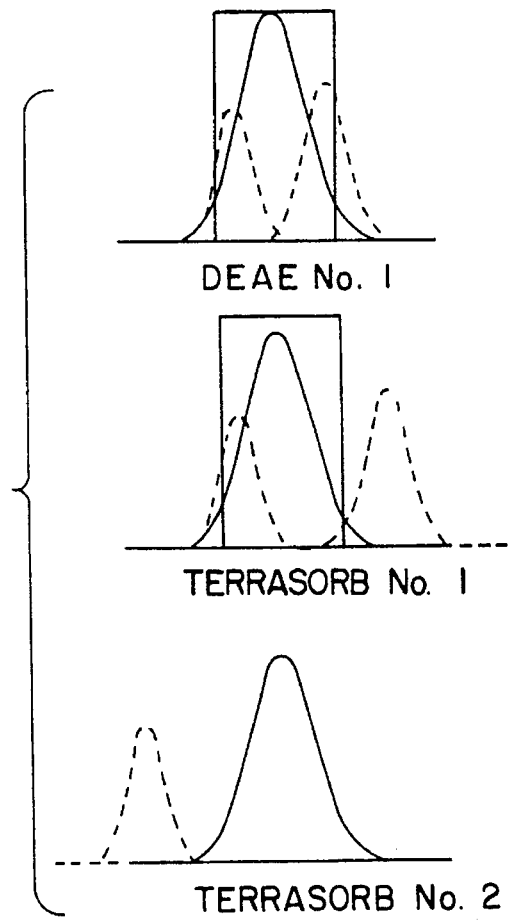
Figure 14:
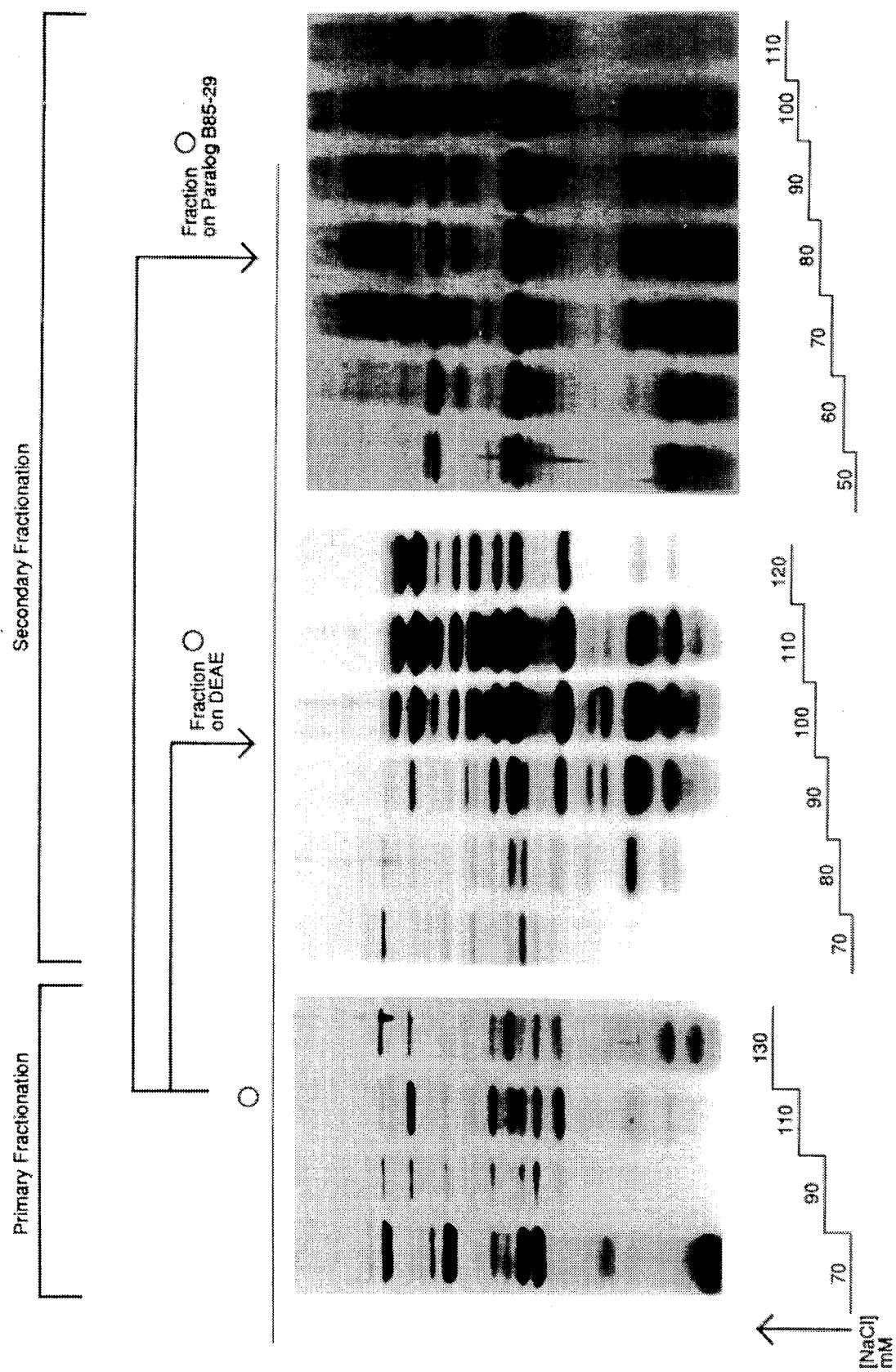
FIG. 14 provides the SDS PAGE analysis of the separations diagrammed in FIG. 13.

FIG. 13 shows that approximately the same results are given for DEAE first and second columns; for the second and third separations of the 90–110 mM fractions on the B85-29 column, however, further separation was obtained. This is also seen by the differing protein patterns obtained by SDS analysis in FIG. 14 where the paralog B85-29 column provides relatively clean separation of at least some of the protein components.

EXAMPLE 6

Comparison of Diversity of a Paralog Panel Versus a Cibacron Panel

Figure 15A:
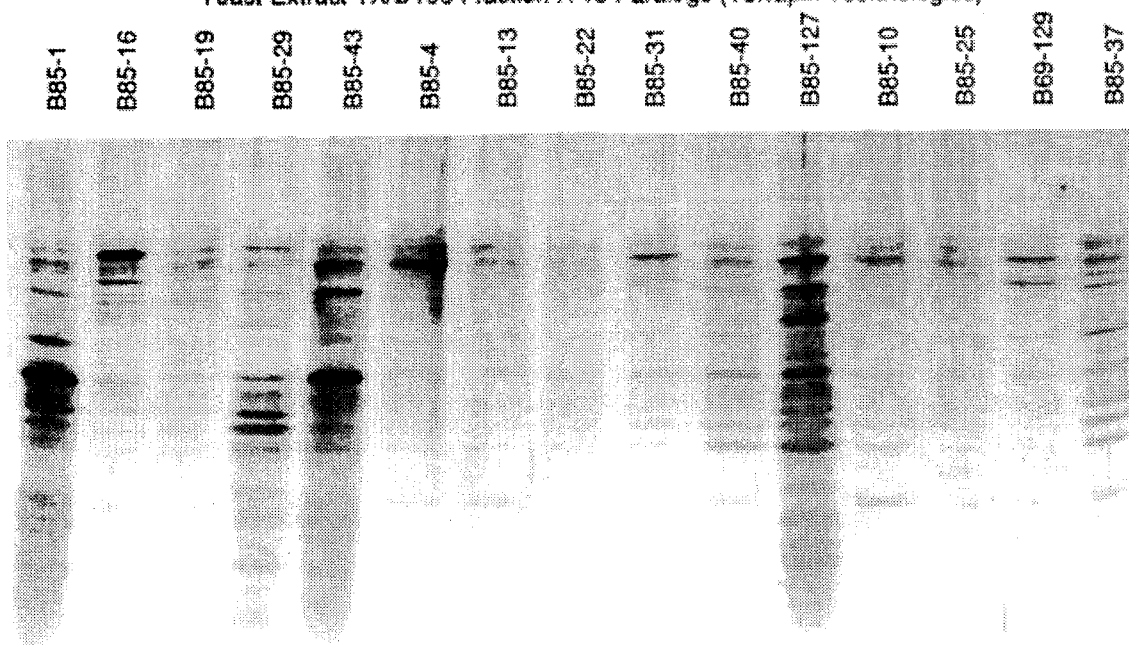
FIG. 15 shows a comparison of a Cibacron panel and a paralog panel with respect to ability to bind proteins of a yeast mixture.
Figure 15B:
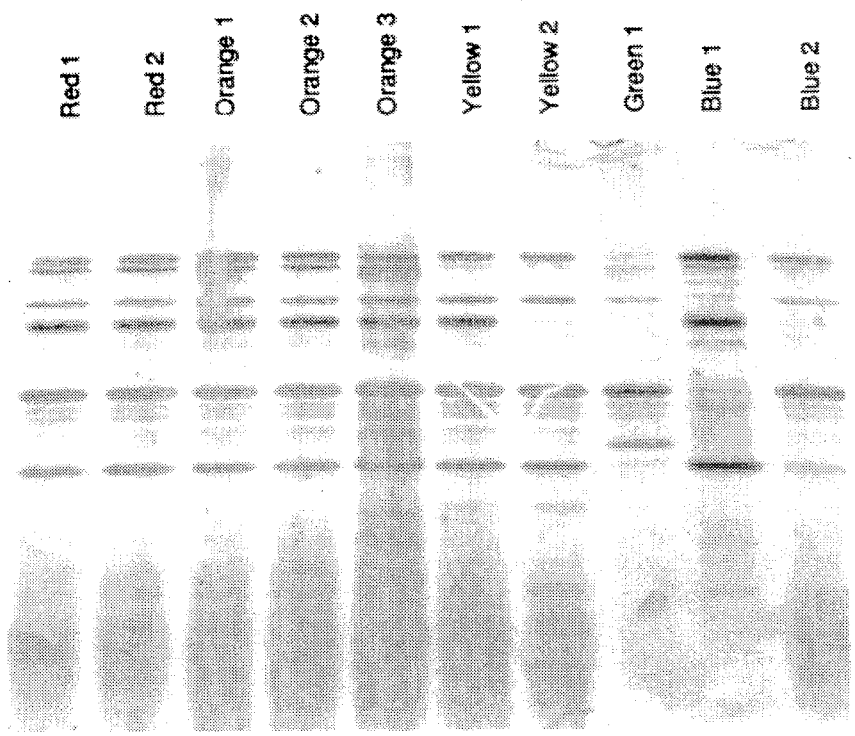

Yeast extract YX/DC-500 was applied to a series of paralog derivatized columns and the eluates assessed by SDS PAGE as described above. A similar determination was made using support coupled to the series of Cibacron dyes contained in ICN Chromatakit®. As shown in FIG. 15B, virtually all of the components of the Cibacron-containing kit showed similar patterns of adsorbed and eluted proteins. Only yellow-2, green-1, blue-1 and blue-2 showed significant differences from the remainder of the components (and from each other) with respect to the various protein bands. As shown in FIG. 15A, a much greater variety of results was obtained using the paralog panel. Further, a larger % of extract binds to one or another paralog than one or another dye indicating a broader range of application for the paralogs.

EXAMPLE 7

Determination of Protein Profiles

The procedure used in Example 6 was repeated using, in place of the YX/DC-500 mixture, an overloading amount of either serum albumin (BSA), cytochrome C, and a series of monoclonal antibodies raised against fluorescein, KLH and the peptide LPDGGY. These samples were loaded onto 15 paralog derivatized Affigel supports in the procedure set forth above. The adsorbed protein was eluted with TE plus 1M NaCl.

Protein concentrations were determined using BioRad Coomassie dye binding assay in the case of cytochrome C and BSA. These results are shown in FIG. 16. The profiles for the two test proteins which are quite different from each other. As shown in the figure (D represents DEAE, C represents CM cellulose, and B represents Affigel 10 blocked with ethanolamine), BSA binds well to paralogs 4, 5 and 11; cytochrome C does not; cytochrome C binds reasonably well to the remaining series of paralogs to which BSA fails to bind; however, reduced binding is found for cytochrome C to paralogs 1 and 2.

Figure 17:
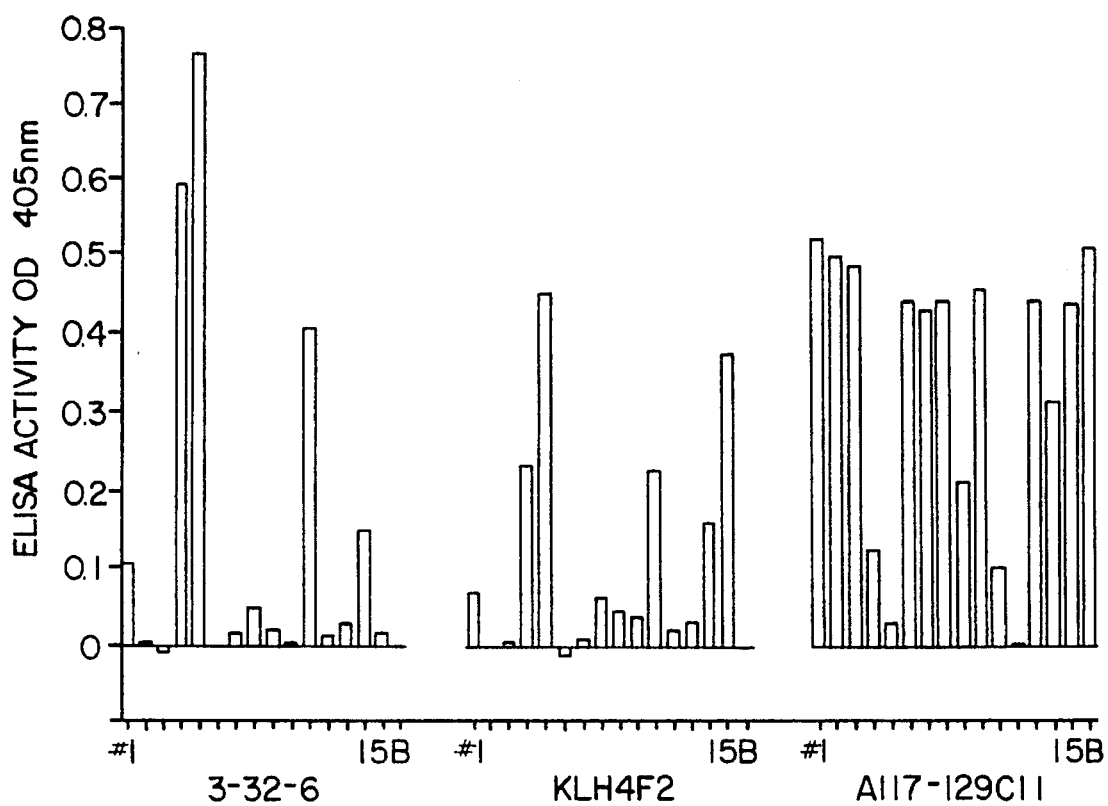
FIG. 17 shows results similar to those of FIG. 16 using a Mab as the single protein.

When monoclonal antibodies were used in this test, an ELISA assay measured the flowthrough and eluted antibodies with detection of the alkaline phosphatase label reaction product by Molecular Devices VMax microplate reader. This measures only nondenatured antibodies. As shown in FIG. 17, all three antibodies give reasonably complex profiles which are different from each other. (The antifluorescein and anti-KLH antibodies are purified IgGs; the anti-LPDGGY is an IgM from culture supernatant containing fetal calf serum.) Such profiles provide a diagnostic test for purification and identification of analyte.

EXAMPLE 8

Determination of Affinity Constant

Figure 18:
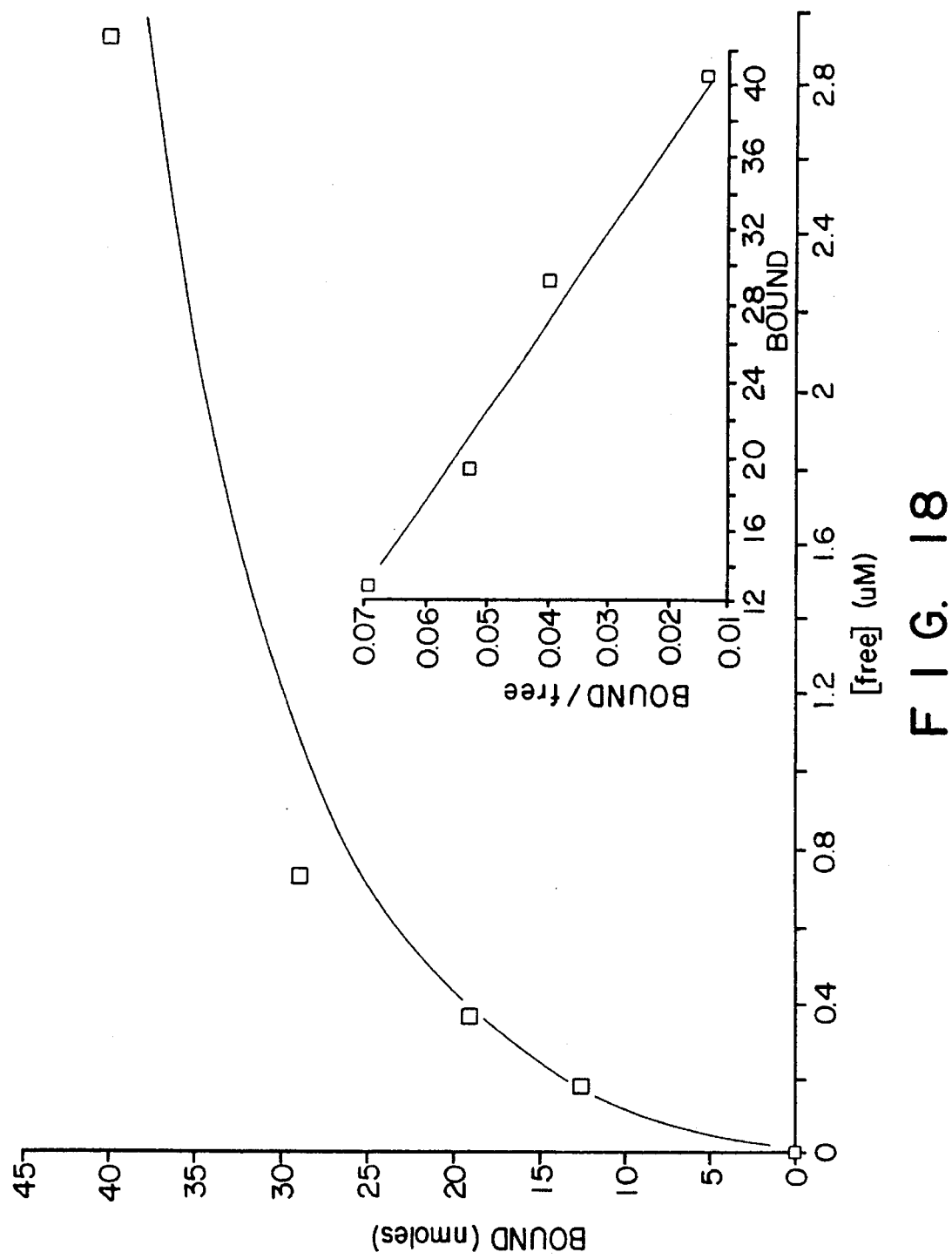
FIG. 18 shows the binding isotherm for bovine serum albumin with respect to paralog B85-29 in determination of the affinity constant.

Using the procedure of Example 7 and paralog B85-29, the binding isotherm for bovine serum albumin was determined by varying initial concentration of the protein applied to the column. As shown in FIG. 18, the value of $2.5 \times 10^6$ $mol^{-1}$ was obtained, which is roughly the same as that for DEAE under the same buffer conditions.

EXAMPLE 9

Paralog Separation Panels for Phenol Pollutants

Figure 19:
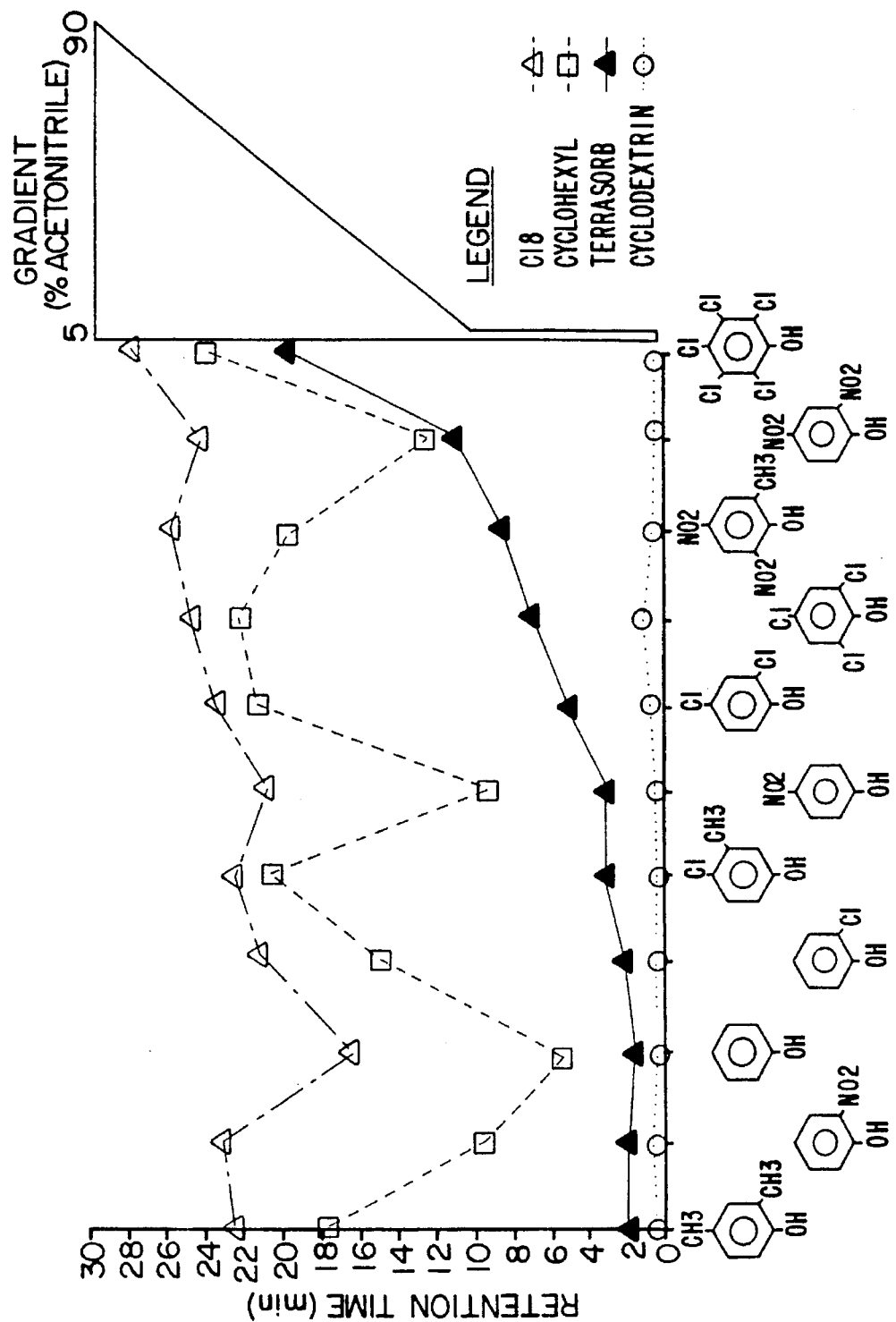
FIG. 19 shows a comparative elution pattern for various chromatographic supports, including a paralog support, with respect to the eleven phenol pollutants identified by the EPA

FIG. 19 shows the ability of various sorbents to separate the 11 phenol pollutants identified by the EPA as environmental hazards. The structures of these phenols are shown in FIG. 19, along with the pattern of elution along an acetonitrile gradient using a variety of sorbents in chromatographic columns. The columns were prepared using CBX beads by conjugating the appropriate paralog to the column. Paralogs used were B69-92 having the structure Gly-Lys-PABA-Phe-PABA-Phe-PABA-Lys; PABA-isoleucine; PABA-alanine; and PABA-methionine. Standard C-18 and cyclohexyl columns, as well as a cyclodextrin column, were used as controls.

As seen in FIG. 19, there is little variation in retention time for these phenols on cyclodextrin columns (open circles; they are not retained at all) or, with the exception of phenol per se, on C-18 columns (22–28 minutes). There is considerable variation when cyclohexyl-derivatized columns are used. The column containing the paralog B69-92 (solid triangles), however, gives a reasonable variety of retention times for a portion of the molecules that are not well discriminated (with the exception of 2,4-dinitrophenol) by the cyclohexyl column.

Figure 20:
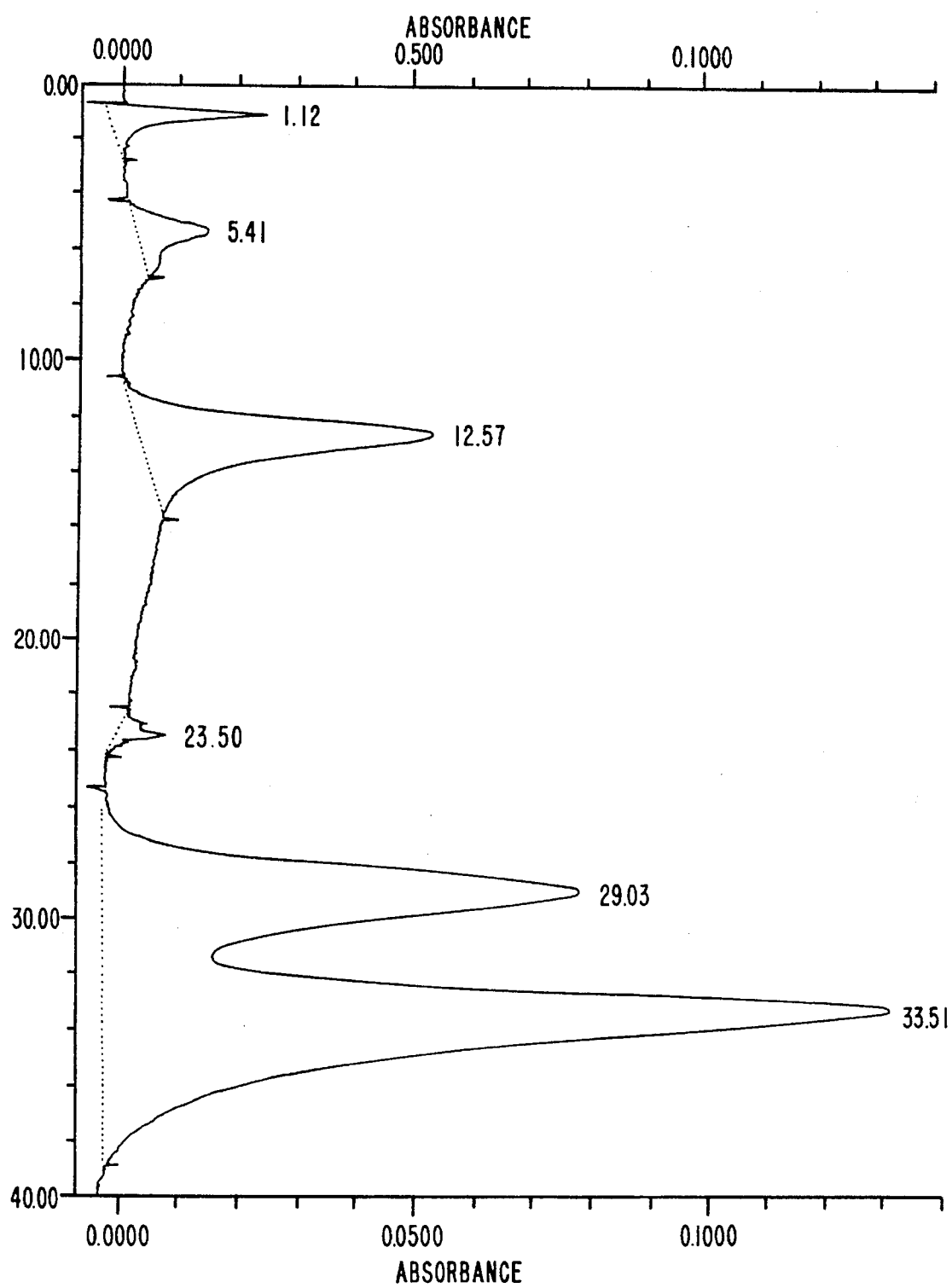
FIGS. 20–22 show elution patterns obtained with the eleven phenol pollutants on three different dipeptide paralogs.
Figure 21:
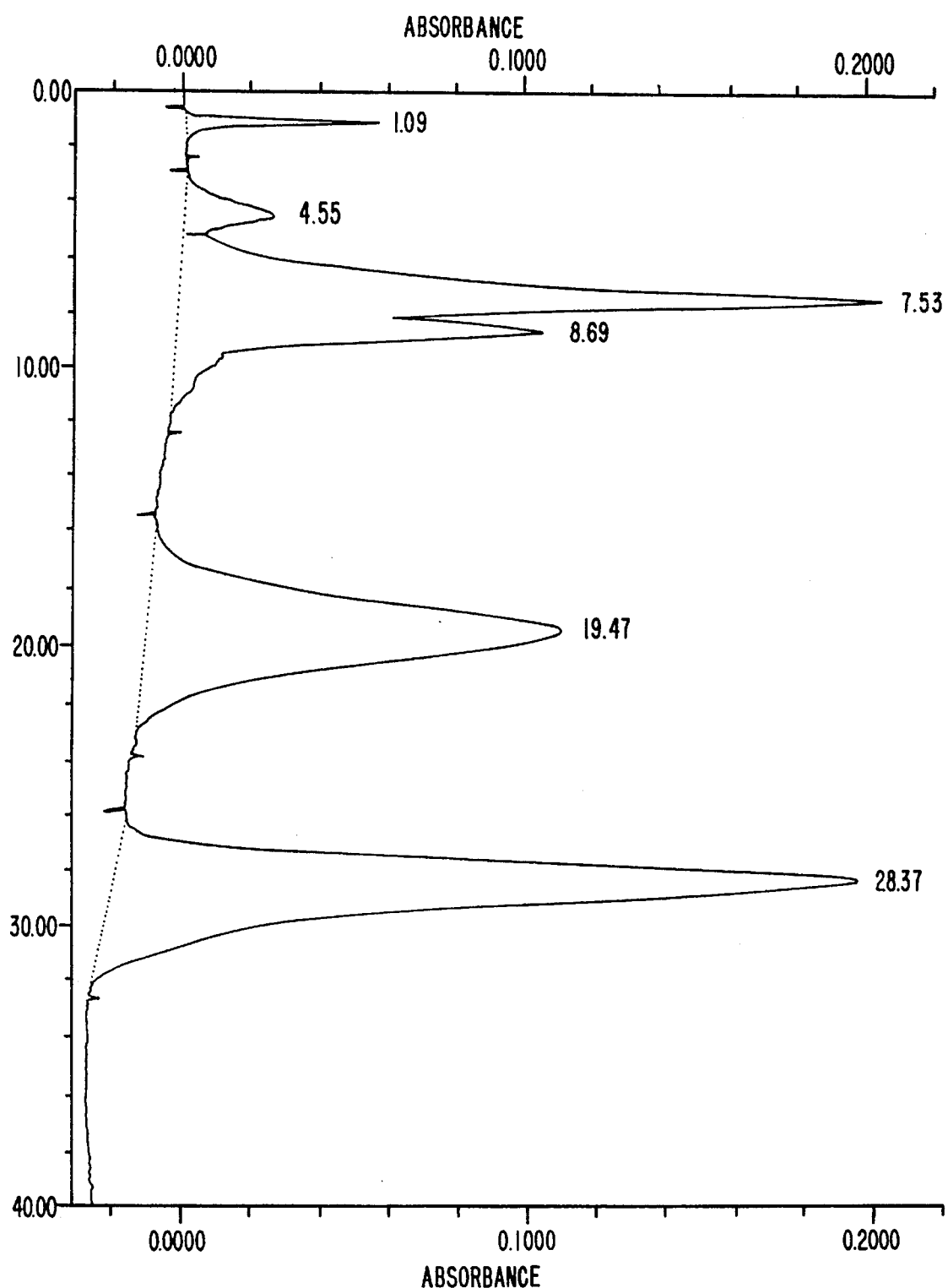
Figure 22:
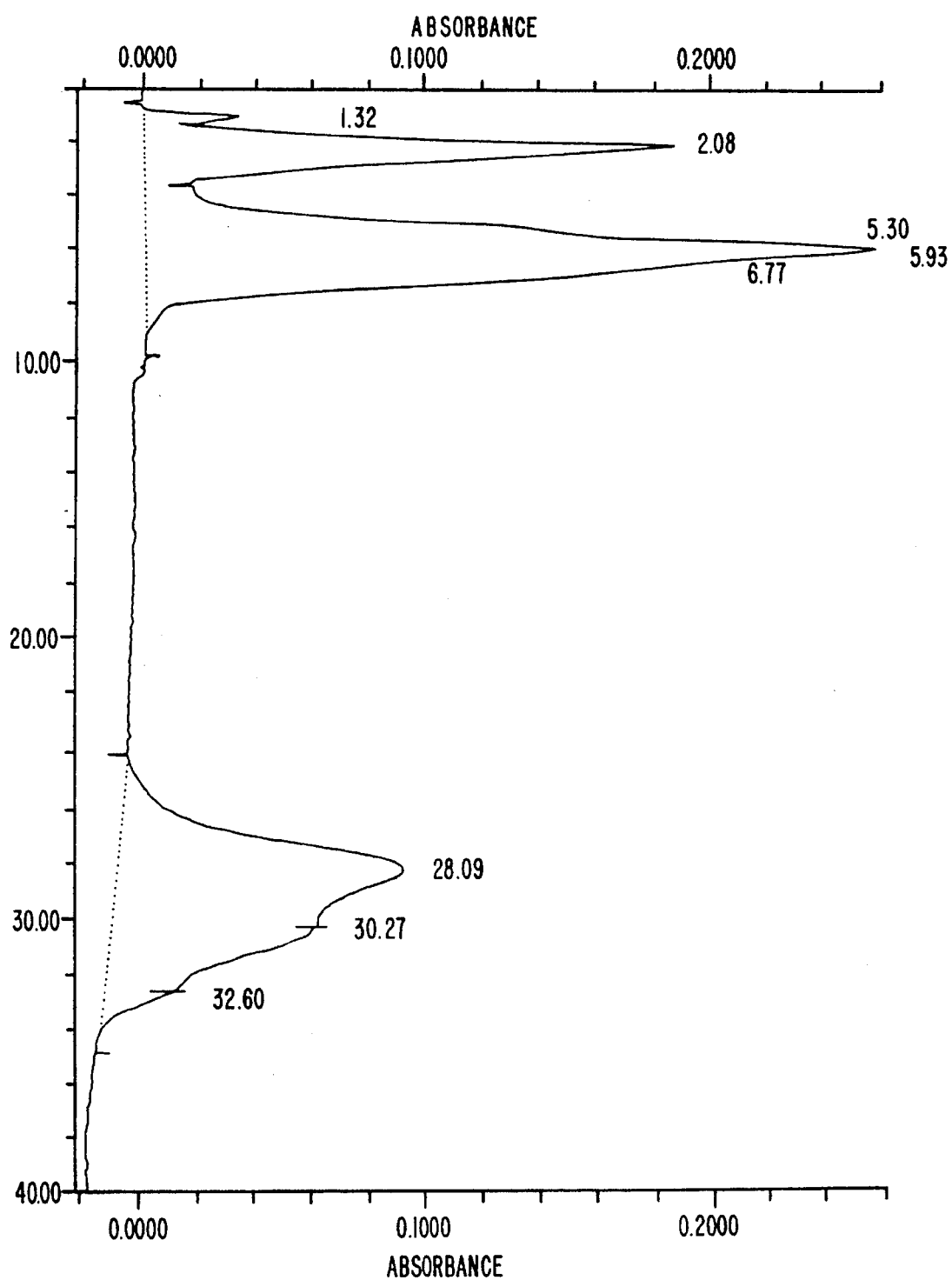

FIGS. 20–22 show the elution patterns for the 11 phenols on three of the above-mentioned paralog-derivatized CBX columns under HPLC conditions. These are PABA-Ile (FIG. 20); PABA-Ala (FIG. 21); and PABA-Met (FIG. 22).

A Beckman HPLC was equipped with a 126 Programmable solvent module and a 168 Diode Array Detector Module, and data processing was done using Beckman System Gold Software Rev. 5.0 on a Tandy 3000NL computer. Solvents of high purity grade were sparged with helium prior to use.

The paralogs were synthesized on 15u CBX silica (J. T. Baker) using carboxylic acid groups on the bonded phase of the CBX beads esterified with N-hyrdoxysuccinimide and EDC. The N-terminal amino acid, dissolved in pH 7.5 PBS was added to the esterified beads to obtain a stable amide bond. The carboxylic acid terminus of the tethered amino acid is esterified and the process repeated to obtain peptide bond formation. The peptides were coupled at 80–100 μmol of bound peptide per gram of silica. "Blocked" columns used as controls were prepared by esterification of the Baker CBX beads followed by addition of ethanolamine.

Columns were prepared by suspending approximately 1.5 grams of column packing material in 10 mL of methanol. A 5 cm×4.6 mm id. column with a 2 μm filter frit was attached to a 20 mL high pressure column packer. The suspension was added to the column packer followed by enough methanol to fill the reservoir. The column was first packed using 160 psi nitrogen gas. The reservoir was refilled; a total of 50 mL of methanol was pressurized over each column, and the column packing apparatus was then attached to an HPLC. Methanol was pumped through the column at a flow rate of 2 mL per minute increasing to 9 mL per minute. When the back pressure stabilized, the column packing was complete.

As seen by a comparison of FIGS. 20–22, quite different elution patterns are obtained, depending on the choice of paralog. Both PABA-isoleucine and PABA-alanine (FIGS. 20 and 21) provide at least six separate peaks among the 11 applied constituents.

An additional comparison using either PABA-Ala or PABA-Ile in comparison with a $C_8$ column is shown in Table A, below. The results show that $C_8$ gives retention times of less than 5 minutes for all of the tested phenols. However, both the PABA-Ala and PABA-Ile columns allow clean separation for at least a substantial number of compounds in this group by providing longer retention times.

TABLE A

| | Elution Time | | | | |
|---|---|---|---|---|---|
| Compound | 0–3 min | 3–5 min | 5–10 min | 10–20 min | >20 min |
| phenol | * | ‡ | | † | |
| 2-nitrophenol | *,†,‡ | | | | |
| 4-nitrophenol | | * | | | †,‡ |
| 2,4-dinitrophenol | * | | † | | ‡ |
| 2,4,6-trinitrophenol | *,† | ‡ | | | |
| 2-chlorophenol | *,‡ | † | | | |
| 2,4-dichlorophenol | *,‡ | | † | | |
| 2,4,6- tri-chlorophenol | *,†,‡ | | | | |
| 2,3,4,5,6-penta chlorophenol | * | | †,‡ | | |

TABLE A-continued

| | Elution Time | | | | |
|---|---|---|---|---|---|
| Compound | 0–3 min | 3–5 min | 5–10 min | 10–20 min | >20 min |
| 3-methyl-4-chlorophenol | * | | †‡ | | |
| 2,4 dimethylphenol | *,‡ | † | | | | where
* = $C_8$
† = PABA-Ala
‡ = PABA-Ile

I claim:

1. A method to identify a paralog which has specific affinity for a first moiety in comparison to additional moieties present in the environment of the first moiety which method comprises:

screening, for ability to selectively bind said first moiety a panel of individual candidate paralogs, wherein said candidate paralogs have systematically varied values of at least two parameters, each of which parameters determines the ability of the paralog to bind to other substances and/or wherein the combination of parameters determines the ability of the paralog to bind to other substances.

2. The method of claim 1 wherein the candidate paralogs of said panel have systematically varied values of at least 3 parameters.

3. The method of claim 2 wherein the candidate peptides of said panel have systematically varied values of at least 4 parameters.

4. The method of claim 3 wherein the candidate peptides of said panel have systematically varied values of at least 5 parameters.

5. The method of claim 1 wherein said parameters are selected from the group consisting of hydrophobic index, isoelectric point, hydrophobic moment, lateral dipole moment, aromaticity index, linear spacing between charged atoms, and corrugation factor.

6. The method of claim 1 wherein the candidate paralogs are linear or cyclic peptides of at least 4 amino acid residues, wherein said peptides may optionally contain modification of one or more peptide linkage to replace said linkage with a linkage selected from the group consisting of —$CH_2NH$—, —$CH_2S$—, —$CH_2CH_2$—, —$CH=CH$ (cis and trans), —$COCH_2$—, —$CH(OH)CH_2$—, and —$CH_2SO$—.

7. The method of claim 6 wherein said paralogs contain 5–15 amino acids.

8. The method of claim 6 wherein said parameters are selected from the group consisting of hydrophobic index, isoelectric point, hydrophobic moment, lateral dipole moment, aromaticity index, linear spacing between charged atoms, and corrugation factor.

9. The method of claim 6 wherein said cyclic peptides are cyclized by formation of a covalent bond selected from the group consisting of a disulfide, an ester, and an amide.

10. The method of claim 6 wherein said cyclic peptides are formed using a bifunctional linker.

11. The method of claim 6 wherein said peptides contain at least one residue selected from the group consisting of para-amino benzoic acid, para-amino cyclohexyl carboxylate, and 1-carboxy-4-aminofuran.

12. The method of claim 1 wherein said candidate paralogs are nucleic acids.

13. The method of claim 12 wherein said parameters are selected from the group consisting of AT/GC ratio, placement of AT and GC on a single strand, number and placement of homopolymeric stretches, dyad asymmetry and palindromic asymmetry.

14. The method of claim 1 wherein said candidate paralogs are synthetic polymers comprised of hydrophilic and hydrophobic monomer units.

15. The method of claim 14 wherein said hydrophobic monomer units provide ethylene chloride residues and said hydrophilic monomeric units provide ethylene glycol residues.

16. The method of claim 1 wherein said candidate paralogs are carbohydrates derivatized with positively and/or negatively charged groups.

17. The method of claim 16 wherein said parameters are selected from the group consisting of isoelectric point, lateral dipole moment and linear distance between charged atoms.

18. The method of claim 16 wherein said carbohydrate is dextran, and said charged groups are sulfate and/or amino groups.

19. The method of claim 1 wherein said candidate paralogs are phosphatidyl diglycerides.

20. The method of claim 1 wherein each of said candidate paralogs further contains a substituent with predetermined specific binding for a target substance.

21. The method of claim 20 wherein said substituent is a boronate residue and the target substance is a carbohydrate or glycoprotein.

22. The method of claim 21 wherein the substituent is an enzyme cofactor; and wherein the target substance is said enzyme.

23. The method of claim 20 wherein said substituent is a substrate analog for an enzyme and the target substance is said enzyme.

24. The method of claim 1 wherein said screening step is conducted by assessing the ability of said first moiety to compete with a labeled mixture, which mixture is capable of binding to all candidate paralogs in the panel, for binding to each candidate paralog in the panel.

25. The method of claim 1 wherein said screening is conducted by passaging sample containing said first moiety through a multiplicity of test portions, each test portion containing a candidate paralog attached to solid support, under conditions wherein specifically binding materials will be adsorbed, recovering an unbound fraction, eluting any adsorbed materials, and detecting the presence or absence of said first moiety in the unbound or eluted material, to determine whether said first moiety shows specific binding to said candidate paralog attached to solid support.

26. The method of claim 25 wherein said test portions are minichromatographic columns.

27. The method of claim 25 wherein said test portions are contained in a membrane-bottomed microtiter plate.

28. The method of claim 1 wherein said screening is conducted by individually testing each candidate paralog for ability to bind said first moiety.

29. The method of claim 1 wherein said panel is prepared by synthesizing individual candidate paralogs according to predetermined values for said parameters over the range of values of said parameters.

30. The method of claim 29 wherein said parameters are selected from the group consisting of hydrophobic index, isoelectric point, hydrophobic moment, lateral dipole moment, aromaticity index, linear spacing between charged atoms, and corrugation factor.

31. The method of claim 1 wherein said panel is prepared by synthesizing a random mixture of said candidate paralogs and sorting said paralogs for ability to bind to a series of ligands, which ligands have systematically varied values of at least two said parameters which determine the ability of the ligand to bind to other substances.

32. The method of claim 1 wherein said panel is prepared by synthesizing a random mixture of said candidate paralogs, sorting said paralogs for ability to bind to a random series of ligands, and retaining only those paralogs which show differing binding profiles with respect to said series of ligands.

* * * * *